United States Patent
Moffitt

(10) Patent No.: US 11,890,480 B2
(45) Date of Patent: Feb. 6, 2024

(54) THERAPY IMPLEMENTED USING DIFFERENT SUB-PERCEPTION NEUROMODULATION TYPES

(71) Applicant: Boston Scientific Neuromodulation Corporation, Valencia, CA (US)

(72) Inventor: Michael A. Moffitt, Solon, OH (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 280 days.

(21) Appl. No.: 16/741,214

(22) Filed: Jan. 13, 2020

(65) Prior Publication Data
US 2020/0147391 A1 May 14, 2020

Related U.S. Application Data

(63) Continuation-in-part of application No. 16/738,786, filed on Jan. 9, 2020, which is a continuation-in-part
(Continued)

(51) Int. Cl.
*A61N 1/36* (2006.01)
*A61N 1/02* (2006.01)

(52) U.S. Cl.
CPC ......... *A61N 1/36167* (2013.01); *A61N 1/025* (2013.01); *A61N 1/36062* (2017.08); *A61N 1/36071* (2013.01); *A61N 1/36132* (2013.01)

(58) Field of Classification Search
CPC .............. A61N 1/36167; A61N 1/025; A61N 1/36062; A61N 1/36071; A61N 1/36132;
(Continued)

(56) References Cited

U.S. PATENT DOCUMENTS 6,181,969 B1  1/2001 Gord
6,516,227 B1  2/2003 Meadows et al.
(Continued)

FOREIGN PATENT DOCUMENTS

CN  202933390  5/2013
EP  2923727  9/2015
(Continued)

OTHER PUBLICATIONS

International Search Report and Written Opinion regarding corresponding PCT Application No. PCT/US2020/013336, dated Apr. 15, 2020.
(Continued)

*Primary Examiner* — Erin M Piateski
*Assistant Examiner* — Ranjani Mari Sundaresan
(74) *Attorney, Agent, or Firm* — Lewis & Reese, PLLC

(57) ABSTRACT

A neuromodulation system for use with electrodes to modulate a volume of neural tissue may include a waveform generator and a controller. The waveform generator may be configured to be electrically connected to the electrodes and provide an electrical waveform through at least some of the electrodes to provide a neuromodulation therapy. The controller may be configured to use a program to control the waveform generator to deliver a neuromodulation therapy by delivering both a fast-acting sub-perception neuromodulation and a slow-acting sub-perception neuromodulation. The fast-acting neuromodulation has a wash-in transition period less than a first time duration, and the slow-acting sub-perception neuromodulation has a wash-in transition period more than a second time duration, the second time duration being longer than the first time duration.

19 Claims, 15 Drawing Sheets

Related U.S. Application Data of application No. 16/657,560, filed on Oct. 18, 2019, which is a continuation-in-part of application No. 16/100,904, filed on Aug. 10, 2018, now Pat. No. 10,576,282, said application No. 16/657,560 is a continuation-in-part of application No. 16/460,655, filed on Jul. 2, 2019, now Pat. No. 11,338,127.

(60) Provisional application No. 62/802,844, filed on Feb. 8, 2019, provisional application No. 62/693,543, filed on Jul. 3, 2018.

(58) Field of Classification Search
CPC ............ A61N 1/36164; A61N 1/37241; A61N 1/0551; A61N 1/37217; A61N 1/3756; A61B 5/053; A61B 5/24
See application file for complete search history.

(56) References Cited

U.S. PATENT DOCUMENTS

| | | |
|---|---|---|
| 7,603,177 B2 | 10/2009 | Sieracki et al. |
| 8,180,451 B2 | 5/2012 | Hickman et al. |
| 8,359,102 B2 | 1/2013 | Alataris et al. |
| 8,515,546 B2 | 8/2013 | Goddard et al. |
| 8,606,362 B2 | 12/2013 | He et al. |
| 8,620,436 B2 | 12/2013 | Parramon et al. |
| 8,712,533 B2 | 4/2014 | Alataris et al. |
| 8,751,009 B2 * | 6/2014 | Wacnik .............. A61N 1/36132 607/59 |
| 8,792,988 B2 | 7/2014 | Alataris et al. |
| 9,259,574 B2 | 2/2016 | Aghassian et al. |
| 9,327,125 B2 | 5/2016 | Alataris et al. |
| 9,333,334 B2 * | 5/2016 | Jeffery .................. A61N 1/0476 |
| 9,333,357 B2 | 5/2016 | Alataris et al. |
| 9,446,243 B2 | 9/2016 | Marnfeldt et al. |
| 9,480,842 B2 | 11/2016 | Alataris et al. |
| 9,789,252 B2 | 10/2017 | Gerber et al. |
| 2010/0023090 A1 | 1/2010 | Jaax et al. |
| 2010/0274312 A1 | 10/2010 | Alataris et al. |
| 2012/0092031 A1 | 4/2012 | Shi et al. |
| 2012/0095519 A1 | 4/2012 | Parramon et al. |
| 2012/0095529 A1 | 4/2012 | Parramon et al. |
| 2013/0053923 A1 | 2/2013 | Jaax et al. |
| 2013/0268026 A1 | 10/2013 | Rao et al. |
| 2014/0277251 A1 | 9/2014 | Gerber et al. |
| 2014/0364919 A1 | 12/2014 | Doan |
| 2015/0080982 A1 | 3/2015 | Funderburk |
| 2015/0231402 A1 | 8/2015 | Aghassian |
| 2015/0335893 A1 | 11/2015 | Parker |
| 2015/0360038 A1 | 12/2015 | Zottola et al. |
| 2016/0082265 A1 | 3/2016 | Moffitt et al. |
| 2016/0114166 A1 | 4/2016 | Kaula et al. |
| 2016/0136429 A1 * | 5/2016 | Massoumi .......... A61N 1/37264 607/59 |
| 2016/0144183 A1 | 5/2016 | Marnfeldt |
| 2016/0158551 A1 | 6/2016 | Kent et al. |
| 2016/0317815 A1 | 11/2016 | Doan et al. |
| 2016/0361543 A1 | 12/2016 | Kaula et al. |
| 2016/0367822 A1 | 12/2016 | Parramon |
| 2017/0056642 A1 | 3/2017 | Moffitt et al. |
| 2017/0106197 A1 | 4/2017 | Wechter et al. |
| 2017/0165490 A1 | 6/2017 | Wechter |
| 2017/0173335 A1 | 6/2017 | Min et al. |
| 2017/0189685 A1 | 7/2017 | Steinke et al. |
| 2017/0348530 A1 | 12/2017 | Doan et al. |
| 2017/0348535 A1 | 12/2017 | Doan et al. |
| 2018/0043172 A1 | 2/2018 | Serrano Carmona |
| 2018/0056078 A1 | 3/2018 | Kashyap et al. |
| 2018/0071513 A1 | 3/2018 | Weiss et al. |
| 2018/0071520 A1 | 3/2018 | Weerakoon et al. |
| 2018/0104493 A1 | 4/2018 | Doan et al. |
| 2018/0214701 A1 | 8/2018 | Zhang et al. |
| 2019/0009094 A1 | 1/2019 | Zhang et al. |
| 2019/0046800 A1 | 2/2019 | Doan et al. |
| 2019/0083796 A1 | 3/2019 | Weerakoon et al. |
| 2019/0175915 A1 | 6/2019 | Brill et al. |
| 2019/0209844 A1 | 7/2019 | Esteller et al. |
| 2019/0290900 A1 | 9/2019 | Esteller et al. |
| 2019/0298992 A1 | 10/2019 | Zhang et al. |
| 2019/0329024 A1 | 10/2019 | Kothandaraman et al. |
| 2019/0329025 A1 | 10/2019 | Moffitt et al. |
| 2019/0329039 A1 | 10/2019 | Marnfeldt et al. |
| 2019/0344083 A1 | 11/2019 | Marnfeldt et al. |
| 2019/0366104 A1 | 12/2019 | Doan et al. |
| 2020/0009367 A1 | 1/2020 | Huertas Fernandez et al. |
| 2020/0009394 A1 | 1/2020 | Huertas Fernandez et al. |

FOREIGN PATENT DOCUMENTS

| | | | |
|---|---|---|---|
| WO | WO-2016109851 A1 * | 7/2016 | ........... A61N 1/0472 |
| WO | 2017/106539 | 6/2017 | |

OTHER PUBLICATIONS

U.S. Appl. No. 62/860,627, Esteller et al., filed Jun. 12, 2019.
U.S. Appl. No. 16/419,879, Doan et al., filed May 22, 2019.
L. Kapural et al., "Novel 10-kHz High-frequency Therapy (HF10 Therapy) Is Superior to Traditional Low-frequency Spinal Cord Stimulation for the Treatment of Chronic Back and Leg Pain," Anesthesiology 2015; 123:851-60 (Oct. 2015).
S. Thomson et al., "The PROCO Randomised Controlled Trial: Effects of Pulse Rate On Clinical Outcomes in Kilohertz Frequency Spinal Cord Stimulation—A Multicentre, Double-blind, Crossover Study," presented at the International Neuromodulation Society (INS) Meeting on May 31, 2017.
E.C. Celik et al., "The effect of low-frequency TENS in the treatment of neuropathic pain in patients with spinal cord injury," Spinal Cord 51:34-337 (2013).
Y. Maeda et al., "Low frequencies, but not high frequencies of bi-polar spinal cord stimulation reduce cutaneous and muscle hyperalgesia induced by nerve injury," Pain 138:143-152 (2008).
S. Thomson et al., "Neural Dosing and Energy Requirements in Kilohertz Frequency Spinal Cord Stimulation (SCS)," poster presented at the International Neuromodulation Society (INS) Meeting on May 31, 2017.
S. Paz et al., "Improved Efficacy of SCS Implants Using Multiple Waveforms and Field Shape Options," poster presented at the International Neuromodulation Society (INS) Meeting on May 31, 2017.
S. Paz et al., "Evaluation of Customized Field Shape for Subperception SCS in a Case Series of Chronic Pain Patients," poster presented at the North American Neuromodulation Society (NANS) Meeting on Jan. 11-14, 2018.
S.J. Thomson et al., "Effects of Rate on Analgesia in Kilohertz Frequency Spinal Cord Stimulation: Results of the PROCO Randomized Controlled Trial," Neuromodulation: Technology at the Neural Interface, vol. 21(1), pp. 67-76 (2018) (published on-line Dec. 8, 2017).
J.M. North et al., "Clinical Outcomes of 1 kHz Subperception Spinal Cord Stimulation in Implanted Patients With Failed Paresthesia-Based Stimulation: Results of a Prospective Randomized Controlled Trial," Neuromodulation: Technology at the Neural Interface, vol. 19(7), pp. 731-737 (2016).
Yearwood, Thomas, et al., Handout titled "A Prospective Comparison of Spinal Cord Stimulation (SCS) Using Dorsal col. Stimulation (DCS), Intraspinal Nerve Root Stimulation (INRS), and Varying Pulse Width in the Treatment of Chronic Low Back Pain," Congress of Neurological Surgeons 56th Annual Meeting, Oct. 7-12, 2006, 2 pages.
Yearwood, Thomas, et al., Poster titled "A Prospective Comparison of Spinal Cord Stimulation (SCS) Using Dorsal col. Stimulation (DCS), Intraspinal Nerve Root Stimulation (INRS), and Varying Pulse Width in the Treatment of Chronic Low Back Pain," Congress of Neurological Surgeons 56th Annual Meeting, Oct. 7-12, 2006, 7 pages.

(56) References Cited

OTHER PUBLICATIONS

Yearwood, Thomas, "Neuropathic Extremity Paid and Spinal Cord Stimulation," Pain Medicine, vol. 7, No. S1, 2006, 6 pages.

* cited by examiner

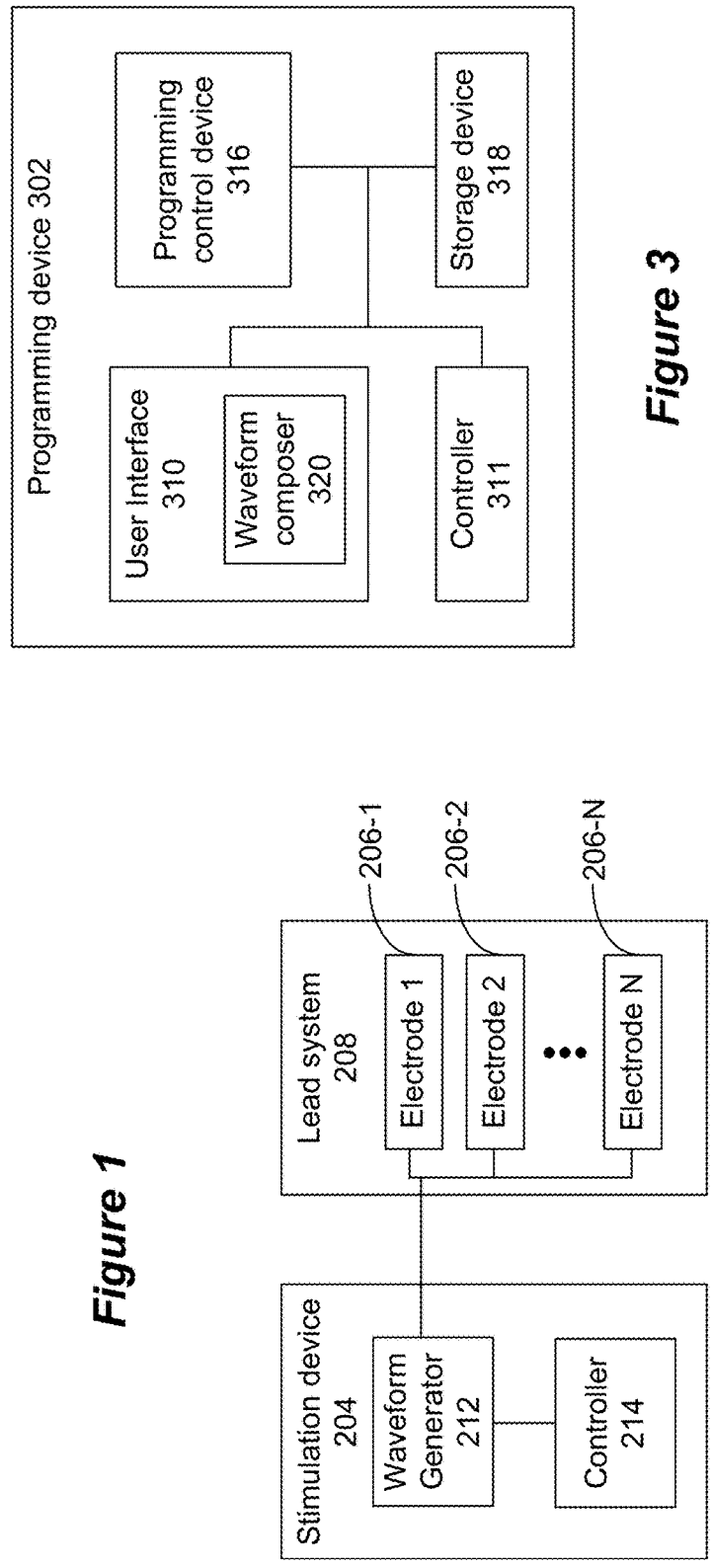
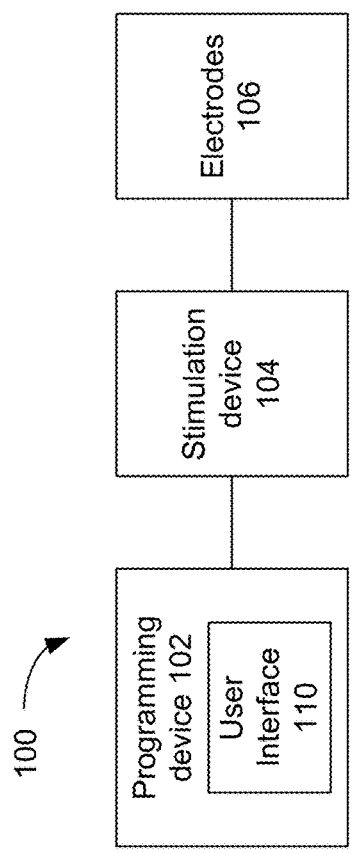
*Figure 1*
*Figure 2*
*Figure 3*

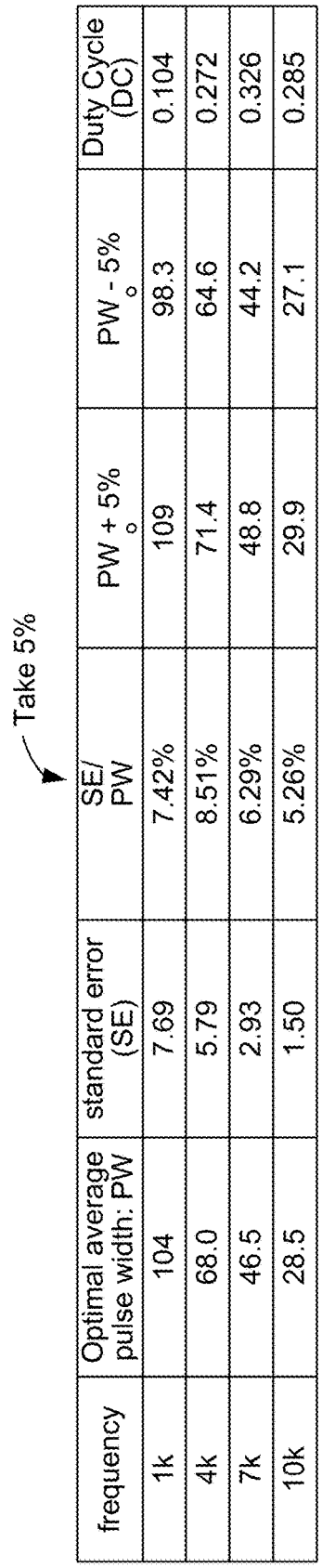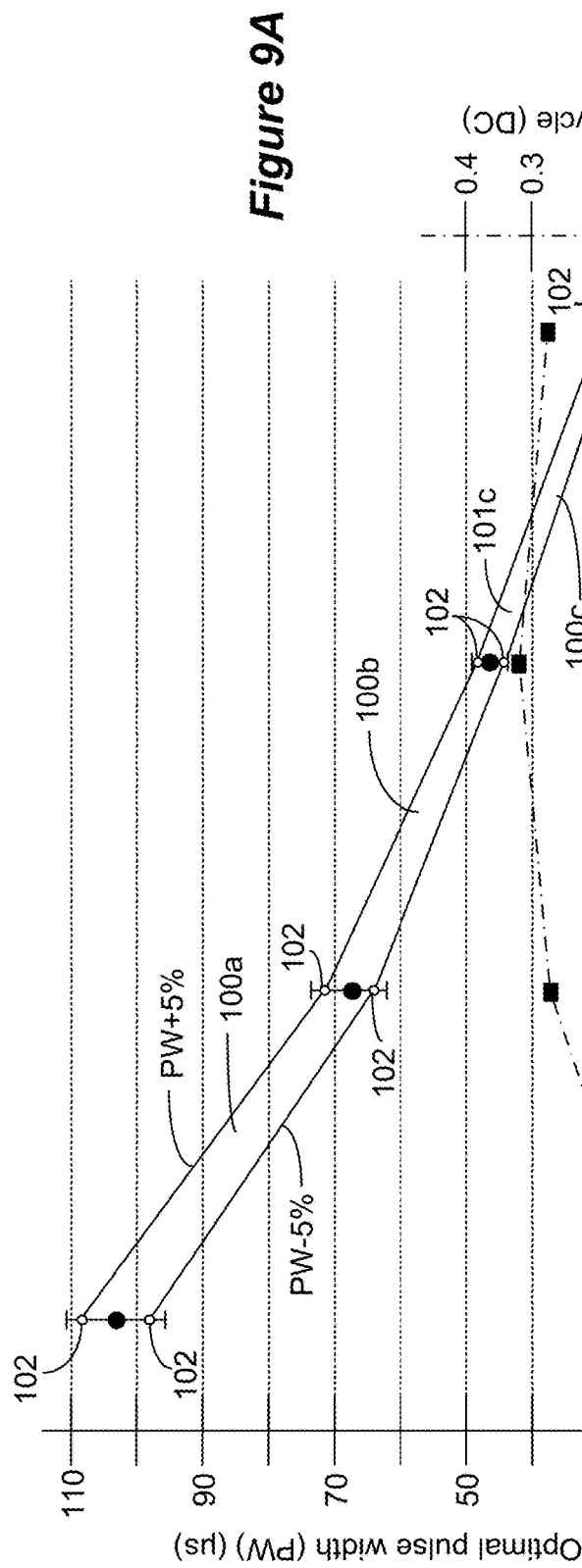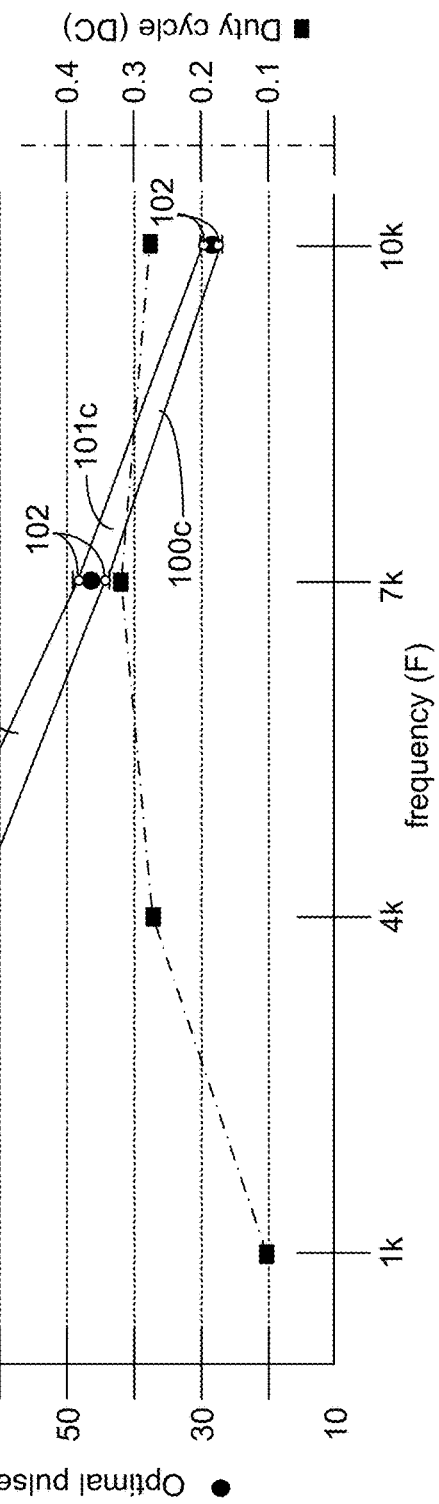
*Figure 9A*

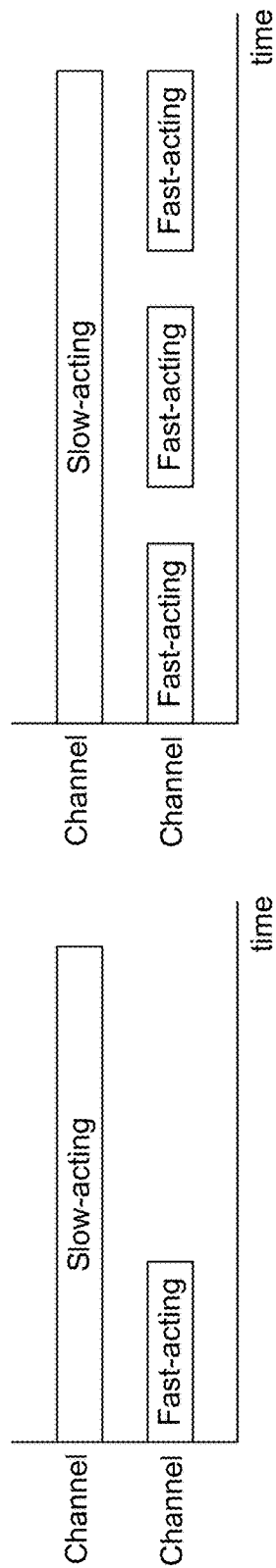

$P1 = F + S1_{A1}$
$P2 = F + S1_{A2}$
$P3 = F + S1_{A3}$
$P4 = F + S2_{A1}$
$P5 = F + S2_{A2}$
$P6 = F + S2_{A3}$
$P7 = F + S3_{A1}$
$P8 = F + S3_{A2}$
$P9 = F + S3_{A3}$ $P1 = F + S1_{A1}$
$S1_{A1}$
$P2 = F + S1_{A2}$
$S1_{A2}$
$P3 = F + S1_{A3}$
$S1_{A3}$
$P4 = F + S2_{A1}$
$S2_{A1}$
$P5 = F + S2_{A2}$
$S2_{A2}$
$P6 = F + S2_{A3}$
$S2_{A3}$
$P7 = F + S3_{A1}$
$S3_{A1}$
$P8 = F + S3_{A2}$
$S3_{A2}$
$P9 = F + S3_{A3}$
$S3_{A3}$

THERAPY IMPLEMENTED USING DIFFERENT SUB-PERCEPTION NEUROMODULATION TYPES

CROSS REFERENCE TO RELATED APPLICATIONS

This application is a non-provisional application of U.S. Provisional Patent Application Ser. No. 62/802,844, filed Feb. 8, 2019.

This application is also a continuation-in-part of U.S. patent application Ser. No. 16/738,786, filed Jan. 9, 2020, which is a continuation-in-part of U.S. patent application Ser. No. 16/657,560, filed Oct. 18, 2019, which is a continuation-in-part of;

U.S. patent application Ser. No. 16/100,904, filed Aug. 10, 2018, which is a non-provisional application of U.S. Provisional Patent Application Ser. No. 62/693,543, filed Jul. 3, 2018;

U.S. patent application Ser. No. 16/460,655, filed Jul. 2, 2019.

Priority is claimed to these above-referenced applications, and all are incorporated by reference in their entireties.

TECHNICAL FIELD

The present disclosure relates generally to medical devices, and more particularly, to neuromodulation systems, devices, and methods.

BACKGROUND

Neuromodulation, also referred to as neurostimulation, has been proposed as a therapy for a number of conditions. Examples of neuromodulation include Spinal Cord Stimulation (SCS), Deep Brain Stimulation (DBS), Peripheral Nerve Stimulation (PNS), and Functional Electrical Stimulation (FES). Implantable neuromodulation systems have been applied to deliver such a therapy. An implantable neuromodulation system may include an implantable neuromodulator, which may also be referred to as an implantable pulse generator (IPG), and one or more implantable leads each including one or more electrodes. The implantable neuromodulator delivers neuromodulation energy through one or more electrodes placed on or near a target site in the nervous system. An external programming device is used to program the implantable neuromodulation with parameters controlling the delivery of the neuromodulation energy. For example, the neuromodulation energy may be delivered in the form of electrical pulses using parameters that specify spatial (where to stimulate), temporal (when to stimulate), and informational (patterns of pulses directing the nervous system to respond as desired) aspects of a pattern of pulses.

SCS has been used to alleviate pain. A therapeutic goal for conventional SCS programming has been to maximize stimulation (i.e., recruitment) of the DC fibers that run in the white matter along the longitudinal axis of the spinal cord and minimal stimulation of other fibers that run perpendicular to the longitudinal axis of the spinal cord (dorsal root fibers, predominantly). The white matter of the DC includes mostly large myelinated axons that form afferent fibers. While the full mechanisms of pain relief are not well understood, it is believed that the perception of pain signals is inhibited via the gate control theory of pain, which suggests that enhanced activity of innocuous touch or pressure afferents via electrical stimulation creates interneuronal activity within the DH of the spinal cord that releases inhibitory neurotransmitters (Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, the large sensory afferents of the DC nerve fibers have been targeted for stimulation at an amplitude that provides pain relief. Current implantable neuromodulation systems typically include electrodes implanted adjacent, i.e., resting near, or upon the dura, to the dorsal column of the spinal cord of the patient and along a longitudinal axis of the spinal cord of the patient.

Activation of large sensory DC nerve fibers also typically creates the paresthesia sensation that often accompanies conventional SCS therapy. Although alternative or artifactual sensations, such as paresthesia, are usually tolerated relative to the sensation of pain, patients sometimes report these sensations to be uncomfortable, and therefore, they can be considered an adverse side-effect to neuromodulation therapy in some cases.

Sub-perception therapy may be used to deliver therapeutically-effective neuromodulation. However, the patient does not perceive the delivery of the neuromodulation energy. For example, a sub-perception SCS therapy may be therapeutically effective to treat pain, for example, but the patient does not sense paresthesia or other sensations caused by the delivery of the neuromodulation energy.

SUMMARY

This Summary includes examples that provide an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

An example (e.g. Example 1) of subject matter (such as a system, a device, apparatus or machine) may be used with electrodes to modulate a volume of neural tissue. The subject matter may include a waveform generator configured to be electrically connected to the electrodes and provide an electrical waveform through at least some of the electrodes to provide a neuromodulation therapy; and a controller configured to use a program to control the waveform generator to deliver a neuromodulation therapy by delivering both a fast-acting sub-perception neuromodulation and a slow-acting sub-perception neuromodulation. The fast-acting neuromodulation has a wash-in transition period less than a first time duration, and the slow-acting sub-perception neuromodulation has a wash-in transition period more than a second time duration, the second time duration being longer than the first time duration.

In Example 2, the subject matter of Example 1 may optionally be configured such that the first time duration is less than 2 hours.

In Example 3, the subject matter of Example 1 may optionally be configured such that the first time duration is less than 30 minutes.

In Example 4, the subject matter of Example 1 may optionally be configured such that the first time duration is less than 2 minutes.

In Example 5, the subject matter of Example 1 may optionally be configured such that the first time duration is less than 30 seconds.

In Example 6, the subject matter of any one or any combination of Examples 1-5 may optionally be configured such that the second time duration is more than two hours.

In Example 7, the subject matter of any one or any combination of Examples 1-5 may optionally be configured such that the second time duration is more than 6 hours.

In Example 8, the subject matter of any one or any combination of Examples 1-5 may optionally be configured such that the second time duration is more than 24 hours.

In Example 9, the subject matter of any one or any combination of Examples 1-5 may optionally be configured such that the system further includes a memory configured to store at least a first programmed modulation parameter set and a second programmed modulation set. The first programmed modulation parameter set may be configured for use to control the waveform generator to provide a slow-acting sub-perception neuromodulation and the second programmed modulation parameter set may be configured for use to control the waveform generator to provide a fast-acting sub-perception neuromodulation.

In Example 10, the subject matter of Example 9 may optionally be configured such that the memory is further configured to store a program schedule to test two or more neuromodulation programs. Each of the two or more neuromodulation programs may include programmed modulation parameter sets to control delivery of a slow-acting sub-perception neuromodulation and fast-acting sub-perception neuromodulation.

In Example 11, the subject matter of Example 10 may optionally be configured such that the programmed modulation parameter sets include programmed modulation parameter sets to provide different slow-acting sub-perception neuromodulation areas.

In Example 12, the subject matter of Example 11 may optionally be configured such that the program schedule is configured for use to deliver slow-acting sub-perception neuromodulation to individual ones of the different slow-acting sub-perception neuromodulation areas for a duration longer than one day.

In Example 13, the subject matter of any one or any combination of Examples 1-12 may optionally be configured such that the programmed modulation parameter sets include programmed modulation parameter sets to provide different slow-acting sub-perception neuromodulation parameters. The different slow-acting sub-perception neuromodulation parameters may include at least one of different amplitudes, different pulse widths, different frequencies, or different patterns. The program schedule may include time periods for reprogramming the fast-acting sub-perception neuromodulation between programs, wherein the reprogramming includes determining a supra-perception neuromodulation parameter set that provides effective supra-perception neuromodulation. The system may further include a user interface configured to receive a user input, and the controller may be further configured to automatically determine a modified fast-acting sub-perception neuromodulation parameter set based on the supra-perception neuromodulation parameter set.

In Example 14, the subject matter of any one or any combination of Examples 1-13 may optionally be configured such that the neuromodulation therapy includes spinal cord neuromodulation to treat chronic pain.

In Example 15, the subject matter of any one or any combination of Examples 1-14 may optionally be configured such that the waveform generator is configured to generate electrical waveforms in timing channels, and the controller is configured to control the waveform generator to, using at least one of the timing channels, deliver both the fast-acting sub-perception neuromodulation and the slow-acting sub-perception neuromodulation.

An example (e.g. Example 16) of subject matter (e.g. a method, a means for performing acts, or a machine-readable medium including instructions that, when performed by the machine, cause the machine to perform acts) may include delivering a neuromodulation therapy by delivering both a fast-acting sub-perception neuromodulation and a slow-acting sub-perception neuromodulation. The fast-acting neuromodulation has a wash-in transition period less than a first time duration, and the slow-acting sub-perception neuromodulation has a wash-in transition period more than a second time duration, the second time duration being longer than the first time duration.

In Example 17, the subject matter of Example 16 may optionally be configured such that the delivering both the fast-acting sub-perception neuromodulation and the slow-acting sub-perception neuromodulation includes delivering spinal cord neuromodulation.

In Example 18, the subject matter of Example 17 may optionally be configured such that the neuromodulation therapy is to treat chronic pain.

In Example 19, the subject matter of any one or any combination of Examples 16-18 may optionally be configured such that the delivering both the fast-acting sub-perception neuromodulation and the slow-acting sub-perception neuromodulation includes delivering the fast-acting sub-perception neuromodulation using a timing channel and delivering the slow-acting sub-perception neuromodulation using the timing channel.

In Example 20, the subject matter of any one or any combination of Examples 16-18 may optionally be configured such that the delivering both the fast-acting sub-perception neuromodulation and the slow-acting sub-perception neuromodulation includes delivering the fast-acting sub-perception neuromodulation using a timing channel and delivering the slow-acting sub-perception neuromodulation using a different timing channel.

In Example 21, the subject matter of any one or any combination of Examples 16-18 may optionally be configured such that the delivering both the fast-acting sub-perception neuromodulation and the slow-acting sub-perception neuromodulation includes initiating the fast-acting sub-perception neuromodulation and the slow-acting sub-perception neuromodulation together.

In Example 22, the subject matter of any one or any combination of Examples 16-18 may optionally be configured such that the delivering both the fast-acting sub-perception neuromodulation and the slow-acting sub-perception neuromodulation includes initiating the fast-acting sub-perception neuromodulation before or after initiating the slow-acting sub-perception neuromodulation.

In Example 23, the subject matter of any one or any combination of Examples 16-18 may optionally be configured such that the delivering both the fast-acting sub-perception neuromodulation and the slow-acting sub-perception neuromodulation includes terminating the fast-acting sub-perception neuromodulation before terminating the slow-acting sub-perception.

In Example 24, the subject matter of any one or any combination of Examples 16-18 may optionally be configured such that the delivering both the fast-acting sub-perception neuromodulation and the slow-acting sub-perception neuromodulation includes intermittently delivering the fast-acting sub-perception neuromodulation multiple times during the slow-acting sub-perception neuromodulation.

In Example 25, the subject matter of any one or any combination of Examples 16-18 may optionally be configured such that a duration of the fast-acting sub-perception neuromodulation is shorter than a duration of the slow-acting sub-perception neuromodulation.

In Example 26, the subject matter of any one or any combination of Examples 16-25 may optionally be configured to further include testing two or more neuromodulation programs according to a program schedule. Each of the two or more neuromodulation programs may include programmed modulation parameter sets to control delivery of a slow-acting sub-perception neuromodulation and fast-acting sub-perception neuromodulation.

In Example 27, the subject matter of Example 26 may optionally be configured such that the programmed modulation parameter sets include programmed modulation parameter sets to provide different slow-acting sub-perception neuromodulation areas.

In Example 28, the subject matter of any one or any combination of Examples 26-27 may optionally be configured such that the program schedule is configured for use to deliver slow-acting sub-perception neuromodulation to individual ones of the different slow-acting sub-perception neuromodulation areas for a duration longer than 12 hours.

In Example 29, the subject matter of any one or any combination of Examples 26-28 may optionally be configured such that the programmed modulation parameter sets include programmed modulation parameter sets to provide different slow-acting sub-perception neuromodulation amplitudes.

In Example 30, the subject matter of any one or any combination of Examples 26-29 may optionally be configured such that the programmed modulation parameter sets provide a same fast-acting sub-perception neuromodulation area.

In Example 31, the subject matter of any one or any combination of Examples 26-30 may optionally be configured to further include intermittently reprogramming the fast-acting sub-perception neuromodulation during the program schedule, wherein the intermittently reprogramming includes determining a supra-perception neuromodulation parameter set that provides effective supra-perception neuromodulation, and responding to a user input by automatically determining a modified fast-acting sub-perception neuromodulation parameter set based on the supra-perception neuromodulation parameter set.

In Example 32, the subject matter of any one or any combination of Examples 16-31 may optionally be configured to further include terminating the fast-acting sub-perception neuromodulation in response to a user input.

In Example 33, the subject matter of any one or any combination of Examples 16-32 may optionally be configured to further include terminating the slow-acting sub-perception neuromodulation in response to a user input.

In Example 34, the subject matter of any one or any combination of Examples 16-33 may optionally be configured such that the delivering the neuromodulation therapy includes responding to a user input by initiating the fast-acting sub-perception neuromodulation or initiating the slow-acting sub-perception neuromodulation.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 1 illustrates, by way of example and not limitation, an embodiment of a neuromodulation system.

FIG. 2 illustrates an example of a stimulation device and a lead system, such as may be implemented in the neuromodulation system.

FIG. 3 illustrates an example of a programming device, such as may be implemented in the neuromodulation system.

FIGS. 9A-9C show further analysis of relationships between average optimal pulse width and frequency in the 1 kHz to 10 kHz frequency range, and identifies statistically significant regions of optimization of these parameters.

FIG. 12 illustrates a combination sub-perception program that may include parameter set(s) to provide slow-acting sub-perception neuromodulation and fast-acting sub-perception neuromodulation.

FIGS. 13-15 illustrate examples of timing for a neuromodulation sub-perception therapy that may include delivering slow-acting and fast-action sub-perception neuromodulation in different timing channels.

DETAILED DESCRIPTION

Figure 5:
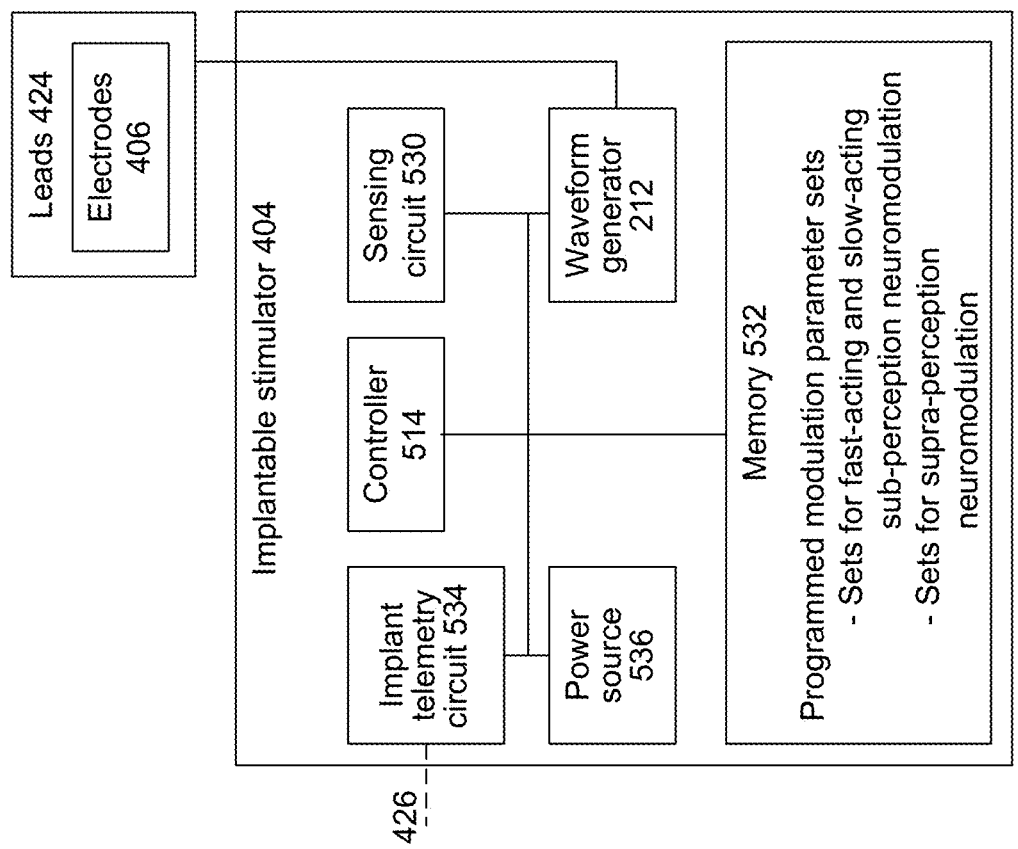
FIG. 5 illustrates, by way of example and not limitation, an example of the implantable stimulator and one or more leads of an implantable neuromodulation system, such as the implantable system.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Neuromodulation therapies typically have a wash-in transition time and a wash-out transition time. A wash-in transition time is a transition period that commences when the neuromodulation therapy is initiated and is complete when maximum therapeutic effects are felt. A wash-out transition time is a transition period that commences when the neuromodulation therapy is turned off and is complete when therapeutic effects are no longer felt.

Supra-perception therapy (e.g. therapy that causes paresthesia) has a short wash-in transition time in so far as the patient experiences paresthesia very quickly after initiating delivery of the neuromodulation energy. In contrast, existing commercialized sub-perception therapies have a long wash-in transition time (e.g. several hours to days). This longer wash-in transition time complicates the evaluation of the therapeutic effectiveness of neuromodulation programs because it may take at least one, two or more days to evaluate one sub-perception therapy program. Thus, conventional sub-perception neuromodulation may be characterized as slow-acting sub-perception neuromodulation. Slow-acting sub-perception neuromodulation has a wash-in time on the order of hours or days. In contrast, fast-acting sub-perception neuromodulation has a wash-in transition time that is much faster than the conventional slow-acting sub-perception neuromodulation. For example, U.S. Patent Application Publication 2019/0046800, which is incorporated herein by reference in its entirety, discusses sub-perception neuromodulation with short wash-in transition times ("fast-acting sub-perception neuromodulation"). However, the fast-acting sub-perception neuromodulation, which may be configured using a paresthesia-based paradigm, may be more sensitive to lead movement than anatomical-based paradigms for configuring sub-perception therapy.

Thus, fast-acting sub-perception neuromodulation may have the positive characteristic of being fast-acting as such fast-acting sub-perception neuromodulation is easier to program, allows more programs to be evaluated in shorter periods of time, and helps patients obtain relief sooner; but fast-acting sub-perception neuromodulation may have the negative characteristic of being susceptible to lead movement as the positioning of the leads and the field seem to be more sensitive, requiring more follow-up programming adjustments to keep the field in the desired location. Slow-acting sub-perception neuromodulation may have the positive characteristic of being less susceptible to lead movement, but may have the negative characteristic of having a slow-wash-in transition time.

Various embodiments described herein provide neuromodulation that captures positive aspects of both fast-acting and slow-acting neuromodulation. For example, various embodiments deliver a neuromodulation therapy by delivering both a fast-acting sub-perception neuromodulation and a slow-acting sub-perception neuromodulation, wherein the fast-acting neuromodulation has a wash-in transition period less than a first time duration, and the slow-acting sub-perception neuromodulation has a wash-in transition period more than a second time duration, where the second time duration is longer than the first time duration. For example, according to some embodiments, fast-acting sub-perception neuromodulation may have a wash-in transition period less than two hours. For some embodiments, fast-acting sub-perception neuromodulation may have a wash-in transition period less than 30 minutes. For some embodiments, fast-acting sub-perception neuromodulation may have a wash-in transition period less than 5 minutes or less than 2 minutes. For some embodiments, fast-acting sub-perception neuromodulation may have a wash-in transition period less than 60 seconds, or less than 40 seconds, or less than 20 seconds. According to some embodiments, slow-acting neuromodulation may have a wash-in transition period more than an hour, or more than two hours. According to some embodiments, slow-acting neuromodulation may have a wash-in transition period more than 6 hours, or more than 12 hours, or more than 18 hours, or more than 24 hours. According to some embodiments, slow-acting neuromodulation may have a wash-in transition period of two or more days. Some embodiments will be described in more detail below, after a brief overview of neuromodulation systems.

FIG. 1 illustrates an example of a neuromodulation system 100. The neuromodulation system 100 may include electrodes 106, a stimulation device 104, and a programming device 102. The electrodes 106 may be configured to be placed on or near one or more neural targets in a patient. The stimulation device 104, which also may be referred to as a neuromodulator, may be configured to be electrically connected to the electrodes 106 and deliver neuromodulation energy, such as in the form of an electrical waveform, to the one or more neural targets though the electrodes 106. The delivery of the neuromodulation may be controlled using a plurality of stimulation parameters, such as stimulation parameters specifying a waveform shape or waveform morphology such as, but not limited to, a pattern of electrical pulses and a selection of electrodes through which each of the electrical pulses may be delivered. At least some parameters of the plurality of stimulation parameters may be programmable by a user, such as a physician or other caregiver who treats the patient using the neuromodulation system 100. Programming device 102 may provide the user with accessibility to the user-programmable parameters. The programming device 102 may be configured to be communicatively coupled to stimulation device 104 via a wired or wireless link. The programming device 102 may receive a signal from the patient and based on the received signal, the programming device 102 may automatically adjust the stimulation parameters, such as to provide improved pain relief to the patient. The received signal may include information about a patient's reaction to delivered neuromodulation energy (e.g. therapeutic effectiveness, side effects, sensation(s) (e.g. paresthesia) to delivering the energy, etc.). In an example where the electrodes may be implanted in the patient, the received signal may include information about the position of the electrodes 106 within the patient.

In some embodiments, the programming device 102 may allow a user to enter various modulation parameters (e.g. frequency, pulse width, amplitude, etc.) used to create a pattern of pulses. The pattern may be a consistent pattern in so far as the values for the modulation parameter(s) do not change, or the pattern may be more complex where the values for the modulation parameter(s) vary. Some waveforms may include multiple pulse patterns and/or multiple pulse shapes. In an example, the programming device 102 may include a user interface that allows the user to set and/or adjust values of the user-programmable parameters by creating and/or editing graphical representations of various waveforms. Such waveforms may include different waveform shapes. The waveform shapes may include regular shapes (e.g. square, sinusoidal, triangular, saw tooth, and the like) or irregular shapes. Such waveforms may include, for example, a pattern of neuromodulation pulses to be delivered to the patient as well as waveform building blocks that may be used in the pattern of neuromodulation pulses. Examples of such waveform building blocks may include pulses, bursts each including a group of the pulses, trains each including a group of the bursts, and sequences each including a group of the pulses, bursts, and trains, as further discussed below. In various embodiments, programming device 102 allows the user to edit existing waveform building blocks, create new waveform building blocks, import waveform building blocks created by other users, and/or export waveform building blocks to be used by other users. The user may also be allowed to define an electrode selection specific to each waveform building block. In the illustrated embodiment, the user interface may include a user interface 110. In various embodiments, the user interface 110 may include a GUI or any other type of user interface accommodating various functions including waveform composition as discussed in this document. In an example, the programming device 102 may receive a waveform file. The waveform file may include a waveform shape or a sequence of waveform building blocks. In an example, the programming device may receive a target location for the neuromodulation energy. The neuromodulation system 100 may deliver an electrical waveform to the received target location, and the electrical waveform may have a shape according to a received waveform file.

FIG. 2 illustrates an example of a stimulation device 204 and a lead system 208, such as may be implemented in the neuromodulation system 100. The stimulation device 204 may represent an example of the stimulation device 104 and may include a waveform generator 212 and a controller 214. The waveform generator 212 may produce and deliver a neuromodulation waveform. Such waveforms may include the same or different waveform shapes. The waveform shapes may include regular shapes (e.g. square, sinusoidal, triangular, saw tooth, and the like) or irregular shapes. The waveforms may include active or passive recharge portions. The controller 214 may control the delivery of the neuromodulation waveform using the plurality of stimulation parameters, which specifies a pattern of the neuromodulation waveform. The lead system 208 may include one or more leads each configured to be electrically connected to stimulation device 204 and a plurality of electrodes 206 distributed in the one or more leads. The plurality of electrodes 206 may include electrode 206-1, electrode 206-2, . . . electrode 206-N, each a single electrically conductive contact providing for an electrical interface between the waveform generator 212 and the tissue of the patient, where N≥2. The neuromodulation waveform may be delivered from waveform generator 212 through a set of electrodes selected from electrodes 206. In an example, the number of leads and the number of electrodes on each lead depend on, for example, the distribution of target(s) of the neuromodulation and the need for controlling the distribution of electric field at each target. In an example, the lead system 208 includes 2 leads each having 8 electrodes.

FIG. 3 illustrates an example of a programming device 302, such as may be implemented in the neuromodulation system 100. The programming device 302 may represent an embodiment of the programming device 102 and may include a storage device 318 (e.g. a memory), a programming control circuit 316, a controller 311 and a user interface 310. The storage device 318 may store various programmed modulation parameter sets. For example, the programmed modulation parameter sets may include parameter set(s) for fast-acting sub-perception neuromodulation, parameter set(s) for slow-acting sub-perception neuromodulation, and parameter set(s) for supra-perception neuromodulation. The storage device 318 may store a plurality of waveform building blocks. The programming control circuit 316 may generate a plurality of stimulation parameters that control the delivery of the neuromodulation waveform according to the pattern of the neuromodulation waveform defined by the parameter set(s). The controller 311 may receive a signal and may adjust the values of the plurality of stimulation parameters based on the received signal. The received signal may include information about a patient sensitivity to delivered neuromodulation (e.g., information about an intensity or location of the delivered neuromodulation). The controller 311 may determine at least one stimulation parameter based on the information about the patient sensitivity. The received signal may include information about a position of an electrode relative to the patient. The electrode may be an implanted electrode within the patient or may be external to the patient. The controller 311 may determine at least one stimulation parameter based on the position of the electrode relative to the patient. The user interface 310 may represent an embodiment of the user interface 110 and allow the user to make parameter adjustments (e.g. adjustments to amplitude, pulse width, frequency, etc.) and/or to compose the waveform building blocks and compose the pattern of the neuromodulation waveform using one or more waveform building blocks selected from the plurality of waveform building blocks.

In an example, the user interface 310 may include a waveform composer 320 that allows the user to manage the parameter set(s) (which may include waveform building blocks), including creating and importing parameter set(s), exporting parameter set(s), and editing parameter set(s). In an example, the user interface 310 may include a GUI that allows for editing parameter set(s). For example, the GUI may allow for graphical editing of each of the waveform building blocks. In an example, the waveform composer 320 may allow the user to compose the pattern of the neuromodulation waveform to be delivered to the patent by the stimulation device 104 using waveform building blocks such as, but not limited to pulses, bursts each including a group of the pulses, trains each including a group of the bursts, and/or sequences each including a group of the pulses, bursts, and trains. In an example, the waveform composer 320 may allow the user to create each waveform building block using one or more waveform building blocks stored in the storage device 318 as templates. In an example, the waveform composer 320 may allow each newly created waveform building block to be saved as an additional waveform building block stored in the storage device 318.

In an example, the user interface 310 may include, but is not limited to, a touchscreen. In an example, the user interface 310 may include any type of presentation device, such as interactive or non-interactive screens, and any type of user input devices that allow the user to edit the waveforms or building blocks and schedule the programs, such as touchscreen, keyboard, keypad, touchpad, trackball, joystick, and mouse. In an example, the circuits of neuromodulation system 100, including its various embodiments discussed in this document, may be implemented using a combination of hardware and software. For example, the circuit of the user interface 110, the controller 214, and the programming control device 316, including their various embodiments discussed in this document, may be implemented using an application-specific circuit constructed to perform one or more particular functions or a general-purpose circuit programmed to perform such function(s). Such a general-purpose circuit may include, but is not limited to, a microprocessor or a portion thereof, a microcontroller or portions thereof, and a programmable logic circuit or a portion thereof.

Figure 4:
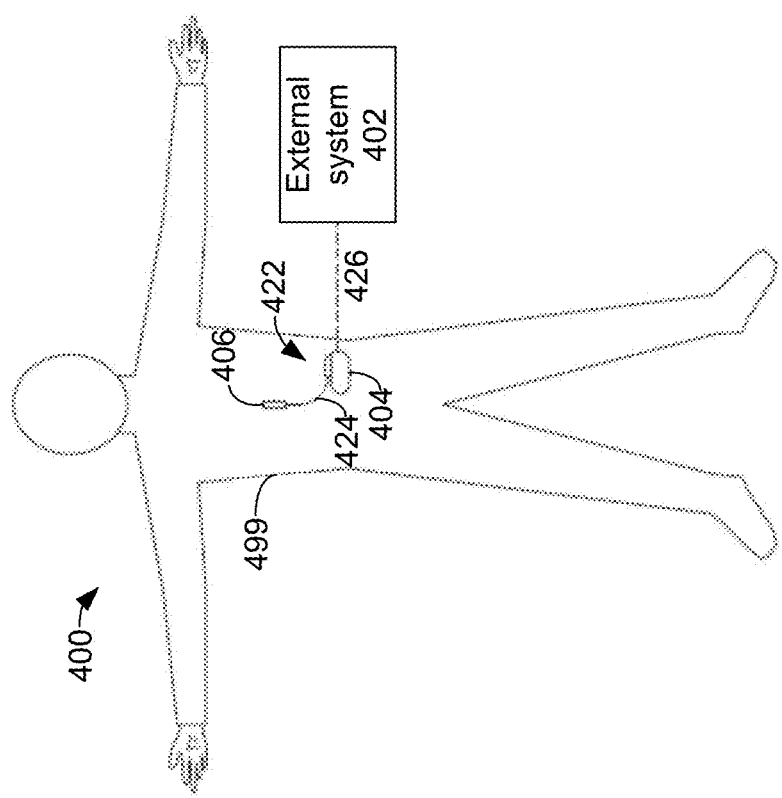
FIG. 4 illustrates, by way of example and not limitation, an implantable neuromodulation system and portions of an environment in which system may be used.

FIG. 4 illustrates, by way of example and not limitation, an implantable neuromodulation system 400 and portions of an environment in which system 400 may be used. The system 400 may include an implantable system 422, an external system 402, and a telemetry link 426 providing for wireless communication between implantable system 422 and external system 402. The implantable system 422 is illustrated in FIG. 4 as being implanted in the patient's body 499. The implantable system 422 may include an implantable stimulator (also referred to as an implantable neuromodulator or an implantable pulse generator (IPG)) 404, a lead system 424, and electrodes 406, which may represent an embodiment of stimulation device 204, lead system 208, and electrodes 206, respectively. The external system 402 may represent an embodiment of programming device 302. In an example, the external system 402 includes one or more external (non-implantable) devices each allowing the user and/or the patient to communicate with implantable system 422. In an example, the external system 402 may include a programming device intended for the user to initialize and adjust settings for the implantable stimulator 404 and a remote control device intended for use by the patient. For example, the remote control device may allow the patient to turn the implantable stimulator 404 on and off and/or adjust certain patient-programmable parameters of the plurality of stimulation parameters. The remote control device may allow the patient to switch among neuromodulation therapies programmed in the implantable stimulator 404, allowing the patient to test the therapeutic effectiveness of neuromodulation therapies. The sizes and shapes of the elements of the implantable system 422 and their location in the body 499 are illustrated by way of example and not by way of restriction. In various examples, the present subject matter may be applied in programming any type of stimulation device that uses electrical waveforms or electrical pulses as stimuli, regardless of stimulation targets in the patient's body and whether the stimulation device is implantable.

FIG. 5 illustrates, by way of example and not limitation, an example of the implantable stimulator 404 and one or more leads 424 of an implantable neuromodulation system, such as the implantable system 422. Implantable stimulator 404 may include a sensing circuit 530 that is optional and used to provide the stimulator with a sensing capability, a waveform generator 212, a controller 514, an memory 532, an implantable telemetry circuit 534, and a power source 536. The sensing circuit 530 may sense one or more physiological signals, such as for the purposes of patient monitoring and/or feedback control of the neuromodulation. Examples of the one or more physiological signals may include neural (e.g. eCAPS) and other signals each indicative of a condition of the patient that is treated by the neuromodulation and/or a response of the patient to the delivery of the neuromodulation. The sensing circuit 530 may sense an impedance of at least one electrode delivering neuromodulation to the patient. The sensing circuit 530 may provide the sensed impedance to the controller 611, such as via the telemetry link 426. The waveform generator 212 may be electrically connected to the electrodes 406 through the lead 424, and may deliver the neuromodulation through a set of electrodes selected from electrodes 406. The controller 514 may represent an embodiment of the controller 214 and may control the delivery of the neuromodulation using the plurality of stimulation parameters. In an example, the controller 514 may control the delivery of the neuromodulation using the one or more sensed physiological signals. The implant telemetry circuit 534 may provide the implantable stimulator 404 with wireless communication with another device such as a device of external system 402, including receiving values of the plurality of stimulation parameters from external system 402. The memory 532 may store values of the plurality of stimulation parameters. For example, the memory 532 may store various programmed modulation parameter sets such parameter set(s) for fast-acting sub-perception neuromodulation, parameter set(s) for slow-acting sub-perception neuromodulation, and parameter set(s) for supra-perception neuromodulation. These parameter set(s) may be organized into therapeutic programs stored in the memory. The power source 536 may provide the implantable stimulator 404 with energy for its operation. In an example, the power source 536 includes a battery. In an example, the power source 536 includes a rechargeable battery and a battery charging circuit for charging the rechargeable battery. The implant telemetry circuit 534 may also function as a power receiver that receives power transmitted from external system 402 through an inductive couple. In various examples, the sensing circuit 530 (if included), the waveform generator 212, the controller 514, the implant telemetry circuit 534, the implant storage device 532, and the power source 536 are encapsulated in a hermetically sealed implantable housing. In various examples, the lead(s) 424 may be implanted such that the electrodes 406 are placed on and/or around one or more targets to which the neuromodulation is to be delivered, while implantable stimulator 404 is subcutaneously implanted and connected to lead(s) 424 at the time of implantation.

Figure 6:
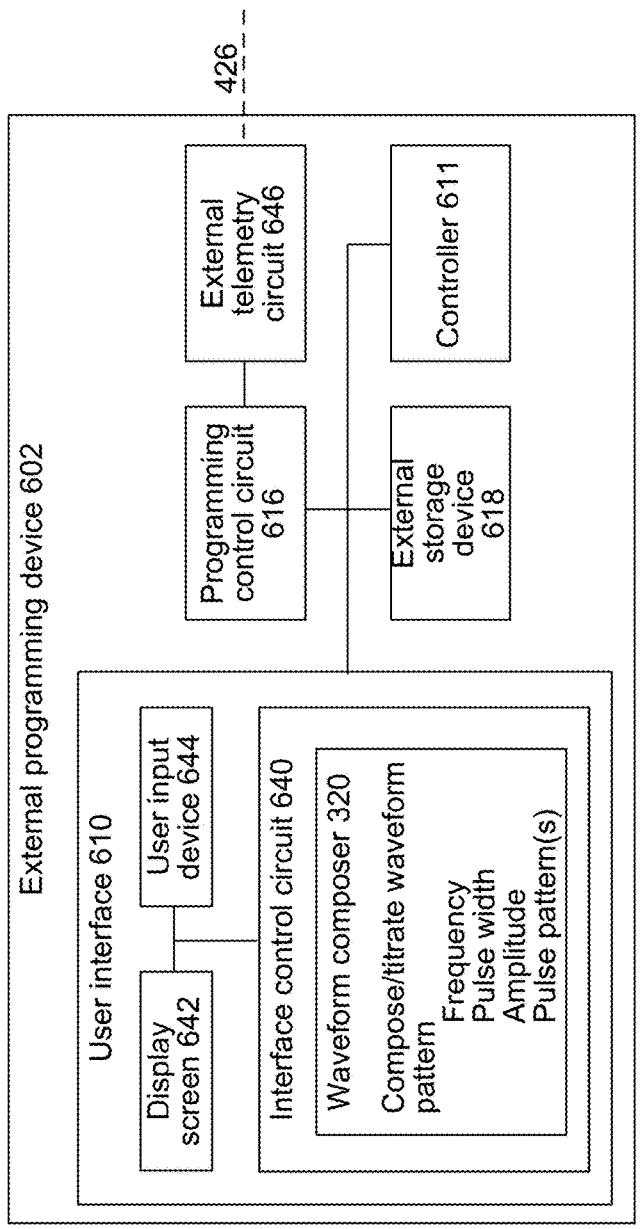
FIG. 6 illustrates an example of an external programming device of an implantable neuromodulation system, such as the external system.

FIG. 6 illustrates an example of an external programming device 602 of an implantable neuromodulation system, such as the external system 402. The external programming device 602 may represent an embodiment of the programming device 302, and may include an external telemetry circuit 646, an external storage device 618, a programming control circuit 616, a controller 611, and a user interface 610.

The external telemetry circuit 646 may provide the external programming device 602 with wireless communication with another device such as the implantable stimulator 404 via telemetry link 426, including transmitting the plurality of stimulation parameters to the implantable stimulator 404. In one embodiment, the external telemetry circuit 646 also transmits power to the implantable stimulator 404 through the inductive couple.

The external storage device 618 may store modulation parameter sets such parameter set(s) for fast-acting sub-perception neuromodulation, parameter set(s) for slow-acting sub-perception neuromodulation, and parameter set(s) for supra-perception neuromodulation. The external storage device 618 may store therapeutic programs that include any one or more of the parameter set(s) (e.g. a fast-acting sub-perception neuromodulation parameter set and a slow-acting sub-perception neuromodulation parameter set). The external storage device 618 may store a plurality of waveform building blocks each selectable for use as a portion of the pattern of the neuromodulation. In various embodiments, each waveform building block of the plurality of waveform building blocks includes one or more waveform shape of the neuromodulation, and may include one or more other waveform building blocks of the plurality of waveform building blocks. Examples of such waveforms include pulses, bursts each including a group of the pulses, trains each including a group of the bursts, and sequences each including a group of the pulses, bursts, and trains. The external storage device 618 may also store a plurality of stimulation fields. Each waveform building block of the plurality of waveform building blocks may associated with one or more fields of the plurality of stimulation fields. Each field of the plurality of stimulation fields may be defined by one or more electrodes of the plurality of electrodes through which the neuromodulation may be delivered and a current distribution of the pulse over the one or more electrodes.

The programming control circuit 616 represents an embodiment of the programming control circuit 316 and may generate the plurality of stimulation parameters, which may be transmitted to the implantable stimulator 404, according to the pattern of the neuromodulation. The pattern may be defined using one or more waveform building blocks selected from the plurality of waveform building blocks stored in the external storage device 618. In various embodiment, the programming control circuit 616 may check values of the plurality of stimulation parameters against safety rules to limit these values within constraints of the safety rules. In an example, the safety rules are heuristic rules.

The user interface 610 may represent an embodiment of the user interface 310 and may allow the user to define the pattern of neuromodulation pulses and perform various other monitoring and programming tasks. In an example, the user interface 610 includes a GUI. The user interface 610 includes a display screen 642, a user input device 644, and an interface control circuit 640. The display screen 642 may include any type of interactive or non-interactive screens, and the user input device 644 may include any type of user input devices that supports the various functions discussed in this document, such as touchscreen, keyboard, keypad, touchpad, trackball, joystick, and mouse. In various examples, the user interface 610 may include element(s) that enable a user to modify values for modulation parameter(s) (e.g. amplitude, frequency, pulse width) and/or may include a GUI that has an interactive screen for displaying a graphical representation of a waveform building block and may allow the user to adjust the waveform building block by graphically editing the waveform building block. The user interface 610 may also allow the user to perform any other functions discussed in this document as may be appreciated by those skilled in the art.

The interface control circuit 640 may control the operation of the user interface 610 including responding to various inputs received by the user input device 644 and defining the one or more stimulation waveforms. The interface control circuit 640 may include the waveform composer 320.

The external programming device 602 may have operation modes including a composition mode and a real-time programming mode. In the composition mode (also known as the pulse pattern composition mode), the user interface 610 may be activated, while the programming control circuit 616 may be deactivated. In an example, the programming control circuit 616 does not dynamically update values of the plurality of stimulation parameters in response to any change in the one or more stimulation waveforms. In the real-time programming mode, both the user interface 610 and the programming control circuit 616 may be activated. The programming control circuit 616 may dynamically update values of the plurality of stimulation parameters in response to changes in the set of one or more stimulation waveforms, and transmit the plurality of stimulation parameters with the updated values to the implantable stimulator 404. The controller 611 may receive a signal and may adjust the values of the plurality of stimulation parameters based on the received signal. The received signal may include information about a patient sensitivity to the stimulation waveform. The controller 611 may determine at least one stimulation parameter based on the information about the patient sensitivity to the stimulation waveform. The received signal may include a sensed impedance received from the sensing circuit 530. The control circuit may determine a relative electrode position based on the received sensed impedance received from the sensing circuit 530. The received signal may include an imaging signal received from an imaging device. The control circuit may determine a relative electrode position based on the received signal from the imaging device. The electrode may be an implanted electrode within the patient or may be external to the patient. The controller 611 may determine at least one stimulation parameter based on the determined relative position of the electrode.

Figure 7:
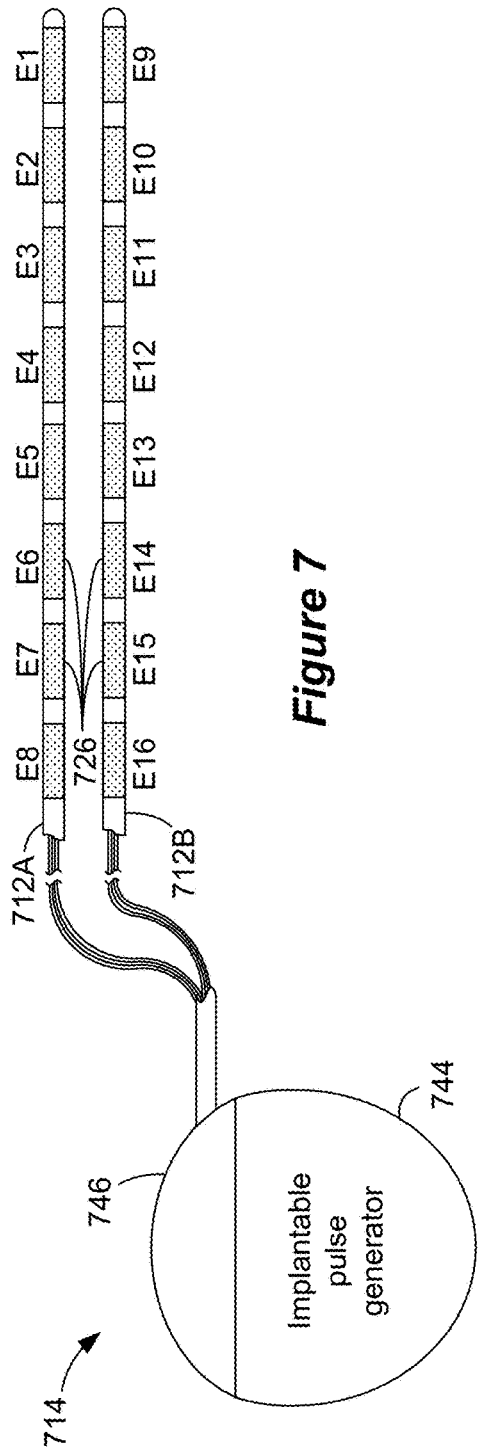
FIG. 7 illustrates, by way of example and not limitation, an example of a profile view of an implantable pulse generator (IPG) and percutaneous leads.

FIG. 7 illustrates, by way of example and not limitation, an example of a profile view of an implantable pulse generator (IPG) 744 and percutaneous leads 712. One of the neuromodulation leads 712a may have eight electrodes 726 (labeled E1-E8), and the other neuromodulation lead 712b may have eight electrodes 726 (labeled E9-E16). The actual number and shape of leads and electrodes may, of course, vary according to the intended application. The IPG 14 may comprise an outer case 744 for housing the electronic and other components (described in further detail below), and a connector 746 to which the proximal ends of the neuromodulation leads 712 mates in a manner that electrically couples the electrodes 726 to the electronics within the outer case 744. The outer case 744 may be composed of an electrically conductive, biocompatible material, such as titanium, and forms a hermetically sealed compartment wherein the internal electronics are protected from the body tissue and fluids. In some examples, the outer case 744 may serve as an electrode.

In an example, the IPG 714 includes a battery and pulse generation circuitry that delivers the electrical modulation energy in the form of one or more electrical pulse trains to the electrode array 726 in accordance with a set of modulation parameters programmed into the IPG 714. Such modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters that may define the pulse amplitude (which may be measured in milliamps or volts depending on whether the IPG 714 supplies constant current or constant voltage to the electrode array 726), pulse duration (which may be measured in microseconds), pulse rate (which may be measured in pulses per second), and burst rate (which may be measured as the modulation on duration X and modulation off duration Y).

In an example, electrical modulation may occur between two (or more) activated electrodes, one of which may be the IPG case 744. Modulation energy may be transmitted to the tissue in a monopolar or multipolar (e.g., bipolar, tripolar, etc.) fashion. Monopolar modulation may occur when a selected one of the lead electrodes 726 is activated along with the case of the IPG 714, so that modulation energy is transmitted between the selected electrode 726 and case. Bipolar modulation may occur when two of the lead electrodes 726 are activated as anode and cathode, so that modulation energy is transmitted between the selected electrodes 726. For example, electrode E3 on the first lead 712$a$ may be activated as an anode at the same time that electrode E11 on the second lead 712$a$ is activated as a cathode. Tripolar modulation may occur when three of the lead electrodes 726 are activated, two as anodes and the remaining one as a cathode, or two as cathodes and the remaining one as an anode. For example, electrodes E4 and E5 on the first lead 712$a$ may be activated as anodes at the same time that electrode E12 on the second lead 712$b$ is activated as a cathode. The modulation energy may be delivered between a specified group of electrodes as monophasic electrical energy or multiphasic electrical energy.

Any of the electrodes E1-E16 and the case electrode may be assigned to up to k possible groups or timing "channels." In one embodiment, k may equal four. The timing channel identifies which electrodes are selected to synchronously source or sink current to create an electric field in the tissue to be stimulated. Amplitudes and polarities of electrodes on a channel may vary. In particular, the electrodes can be selected to be positive (anode, sourcing current), negative (cathode, sinking current), or off (no current) polarity in any of the k timing channels.

As mentioned earlier, U.S. Patent Application Publication 2019/0046800 discusses sub-perception neuromodulation with short wash-in transition times ("fast-acting sub-perception neuromodulation"). The following discussion from that application discusses search methods for finding parameter values for parameter sets that may provide fast-acting sub-perception neuromodulation.

Sweet spot searching, and in particular supra-perception sweet spot searching, may be used to determine the electrodes to be used during subsequent sub-perception therapy, it should be noted that this is not strictly necessary. Sub-perception therapy can be preceded by sub-perception sweet spot searching, or may not be preceded by sweet spot searching at all. The sub-perception therapy as described next is not reliant on the use of any sweet spot search.

Testing of SCS patients have suggested that statistically significant correlations exist between pulse width (PW) and frequency (F) where an SCS patient will experience a reduction in back pain without paresthesia (sub-perception). Use of this information can be helpful in deciding what pulse width is likely optimal for a given SCS patient based on a particular frequency, and in deciding what frequency is likely optimal for a given SCS patient based on a particular pulse width. This information suggests that paresthesia-free sub-perception SCS stimulation can occur at frequencies of 10 kHz and below. Use of such low frequencies allows sub-perception therapy to be used with much lower power consumption in the patient's implantable pulse generator (IPG) or external trial stimulator (ETS).

Patients were tested at frequencies within a range of 1 kHz to 10 kHz. Patients with back pain, but not yet receiving SCS therapy, were first identified. Key patient inclusion criteria included having persistent lower back pain for greater than 90 days; a NRS pain scale of 5 or greater (NRS is explained below); stable opioid medications for 30 days; and a Baseline Oswestry Disability index score of greater than or equal to 20 and lower than or equal to 80. Key patient exclusion criteria included having back surgery in the previous 6 months; existence of other confounding medical/psychological conditions; and untreated major psychiatric comorbidity or serious drug related behavior issues.

After such initial screening, patients periodically entered a qualitative indication of their pain (i.e., a pain score) into a portable e-diary device. Such pain scores can comprise a Numerical Rating Scale (NRS) score from 1-10, and were input to the e-diary three times daily. As shown in FIG. 8C, the baseline NRS score for patients not eventually excluded from the study and not yet receiving sub-perception stimulation therapy was approximately 6.75/10, with a standard error, SE (sigma/SQRT(n)) of 0.25.

Patients then had trial leads implanted on the left and right sides of the spinal column, and were provided external trial stimulation. Patients were excluded from the study if SCS therapy was not helpful. Those patients for whom external trial stimulation was helpful eventually received full implantation of a permanent IPG. After a healing period, a "sweet spot" for stimulation was located in each patient, i.e., which electrodes should be active (E) and with what polarities (P) and relative amplitudes (X %) to recruit and thus treat a site of neural site in the patient. The sweet spot search may occur in any of the manners (e.g. moving monopolar or bipolar or multipolar stimulation via actual electrodes or virtual poles using sub-perception or supra-perception stimulation.

During sweet spot searching, bipolar stimulation using only two electrodes was used for each patient, and using only adjacent electrodes on a single. If a patient had sweet spot electrodes in the desired thoracic location and if they experienced a 30% or greater pain relief per an NRS score, such patients were continued in the study; patients not meeting these criteria were excluded from further study. While the study started initially with 39 patients, 19 patients were excluded from study, leaving a total of 20 patients remaining.

The remaining 20 patients were then subjected to a "washout" period, meaning their IPGs did not provide stimulation for a time. Specifically, patients' NRS pain scores were monitored until their pain reached 80% of their initial baseline pain. This was to ensure that previous benefits of stimulation did not carry over to a next analysis period.

Thereafter, remaining patients were subjected to sub-perception SCS therapy at different frequencies in the range from 1 kHz to 10 kHz using the sweet spot active electrodes determined earlier. The patients were each tested using stimulation pulses with frequencies of 10 kHz, 7 kHz, 4 kHz, and 1 kHz. The frequencies were applied to each patient in random orders. Testing at a given frequency, once complete, was followed by a washout period before testing at another frequency began.

At each tested frequency, the amplitude (A) and pulse width (PW) of the stimulation was adjusted and optimized for each patient such that each patient experienced good pain relief possible but without paresthesia (sub-perception). Each patient was stimulated at a low amplitude (e.g., 0), which amplitude was increased to a maximum point (perception threshold) where paresthesia was noticeable by the patient. Initial stimulation was then chosen for the patient at 50% of that maximum amplitude, i.e., such that stimulation was sub-perception and hence paresthesia free. However, other percentages of the maximum amplitude (80%, 90%, etc.) could be chosen as well, and can vary with patient activity or position, as explained further below. In one example, the stimulation circuitry is configurable to receive an instruction from the GUI via a selectable option to reduce the amplitude of the stimulation pulses to or by a set amount or percentage to render the so that the pulses can be made sub-perception if they are not already. Other stimulation parameters may also be reduced (e.g., pulse width, charge) to the same effect.

The patient would then leave the clinician's office, and thereafter and in communication with the clinician (or her technician or programmer) would make adjustments to his stimulation (amplitude and pulse width) using his external controller. At the same time, the patient would enter NRS pain scores in his e-diary (e.g., the external controller), again three times a day. Patient adjustment of the amplitude and pulse width was typically an iterative process, but essentially adjustment were attempted based on feedback from the patient to adjust the therapy to decrease their pain while still ensuring that stimulation was sub-perception. Testing at each frequency lasted about three weeks, and stimulation adjustments might be made every couple of days or so. At the end of the testing period at a given frequency, optimal amplitude and pulse widths had been determined and were logged for each patient, along with patient NRS pain scores for those optimal parameters as entered in their e-diaries.

In one example, the percentage of the maximum amplitude used to provide sub-perception stimulation could be chosen dependent on an activity level or position of the patient. In regard, the IPG or ETS can include means for determining patient activity or position, such as an accelerometer. If the accelerometer indicates a high degree of patient activity or a position where the electrodes would be farther away from the spinal cord (e.g., lying down), the amplitude could be increased to a higher percentage to increase the current (e.g., 90% of the maximum amplitude). If the patient is experiencing a lower degree of activity or a position where the electrodes would be closer to the spinal card (e.g., standing), the amplitude can be decreased (e.g., to 50% of the maximum amplitude). Although not shown, the GUI of the external device can include an option to set the percentage of the maximum amplitude at which paresthesia become noticeable to the patient, thus allowing the patient to adjust the sub-perception current amplitude.

Preferably, Multiple Independent Current Control (MICC) is used to provide or adjust the sub-perception therapy. This allows the current at each electrode to be independently set, which promotes the steering of current or charge between electrodes, facilitates the formation of virtual bipoles, and more generally allows the electric field to be shaped in the patient's tissue. In particular, MICC, can be used to steer sub-perception therapy to different locations in the electrode array and thus the spinal cord. For example, once a set of sub-perception stimulation parameters has been chosen for the patient, one or more of the stimulation parameters can be changed. Such changes may be warranted or dictated by the therapy location. The physiology of the patient may vary at different vertebral positions, and tissue may be more or less conductive at different therapy locations. Therefore, if the sub-perception therapy location is steered to a new location along the spinal cord (which location change may comprise changing the anode/cathode distance or focus), it may be warranted to adjust at least one of the stimulation parameters, such as amplitude. Adjustment to sub-perception therapy can also include varying other stimulation parameters, such as pulse width, frequency, and even the duration of the interphase period (IP).

The interphase duration can impact the neural dose, or the rate of charge infusion, such that higher sub-perception amplitudes would be used with shorter interphase durations. In one example, the interphase duration can be varied between 0-3 ms. After a washout period, a new frequency was tested, using the same protocol as just described.

Figure 8B:
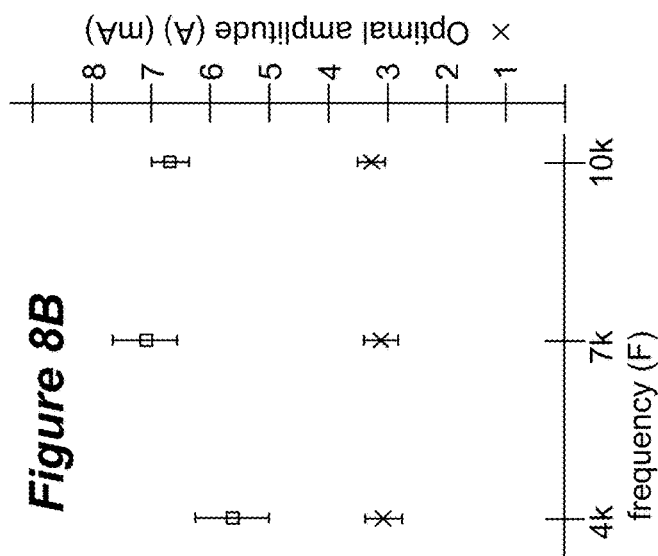
FIGS. 8A-8C show various results of the study as a function of stimulation frequency in the 1 kHz to 10 kHz frequency range, including average optimal pulse width (FIG. 8A), mean charge per second and optimal stimulation amplitude (FIG. 8B), and back pain scores (FIG. 8C).
Figure 8A:
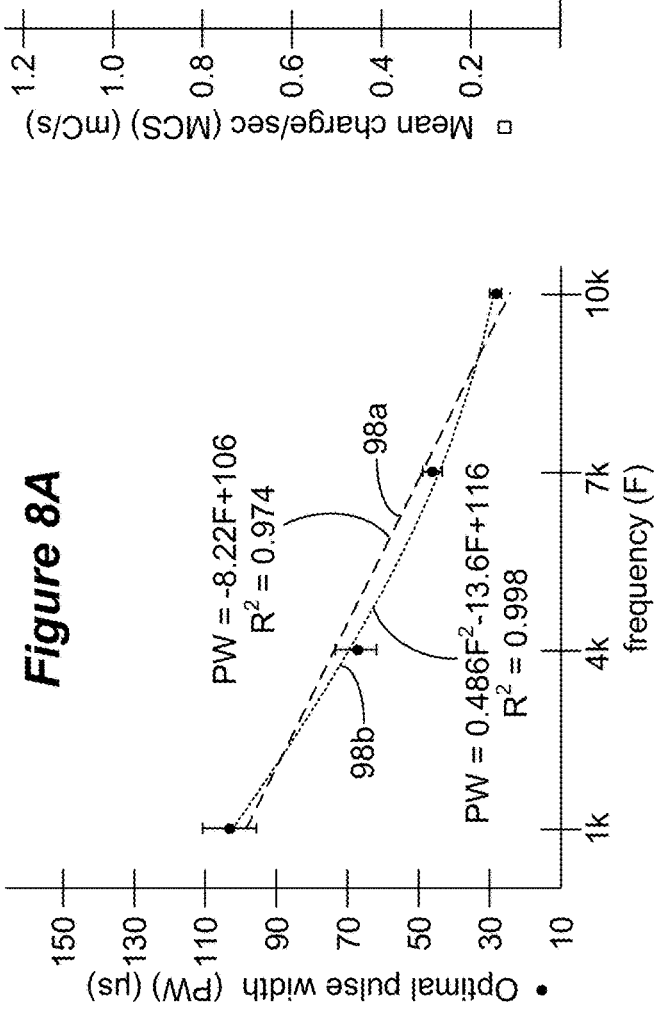
Figure 8C:
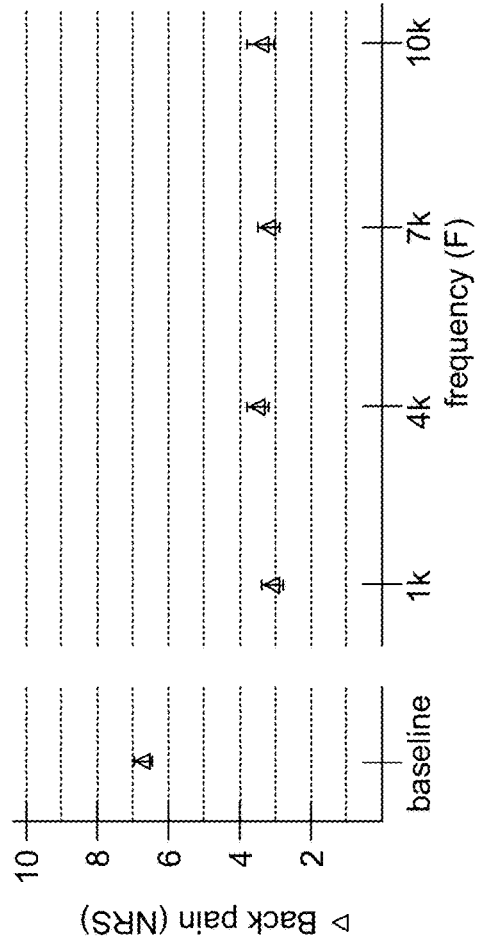

FIGS. 8A-8C show the results of testing the patients at 10 kHz, 7 kHz, 4 Hz and 1 kHz. Data is shown in each figure as average values for the 20 remaining patients at each frequency, with error bars reflecting standard error (SE) between the patients.

Starting with FIG. 8B, the optimized amplitude A for the 20 remaining patients are shown at the tested frequencies. The optimal amplitude at each frequency was essentially constant—around 3 mA. FIG. 8B also shows the amount of energy expended at each frequency, more specifically a mean charge per second (MCS) (in mC/s) attributable to the pulses. MCS is computed by taking the optimal pulse width (FIG. 8, discussed next) and multiplying it by the optimal amplitude (A) and the frequency (F), which MCS value can comprise a neural dose. MCS correlates to the current or power expended to form the optimal pulses. Significantly, the MCS is significantly lower at lower frequencies: for example, the MCS at F=1 kHz is approximately ⅓ of its value at higher frequencies (e.g., F=7 kHz or 10 kHz). This means that optimal SCS therapy—that alleviates back pain without paresthesia—is achievable at lower frequencies like F=1 kHz, with the added benefit of lower power draws that are more considerate of the IPG 10's (or ETS 40's) battery.

FIG. 8A shows optimal pulse width as a function of frequency for the 1 kHz to 10 kHz frequency range tested. As shown, the relationship follows a statistically significant trend: when modeled using linear regression 98$a$, PW=−8.22F+106, where pulse width is measured in microseconds and frequency is measured in kiloHertz, with a correlation coefficient $R^2$ of 0.974; when modeled using polynomial regression 98$b$, PW=0.486$F^2$−13.6F+116, again with pulse width measured in microseconds and frequency measured in kiloHertz, with an even better correlation coefficient of $R^2$=0.998. Other fitting methods could be used to establish other information relating frequency and pulse width at which stimulation pulses are formed to provide pain relief without paresthesia in the frequency range of 1 kHz to 10 kHz.

Note that the relationship between optimal pulse width and frequency is not simply an expected relationship between frequency and duty cycle (DC), i.e., the duration that a pulse is 'on' divided by its period (1/F). In this regard, notice that a given frequency has a natural effect on pulse width: one would expect that a higher frequency pulses would have smaller pulse widths. Thus, it might be expected for example that a 1 kHz waveform with a 100 microsecond pulse width would have the same clinical results as a 10 kHz waveform with a 10 microsecond frequency, because the duty cycle of both of these waveforms is 10%. FIG. 9A shows the resulting duty cycle of the stimulation waveforms using the optimal pulse width in the frequency range of 1 kHz to 10 kHz. Here, duty cycle is computed by considering the total 'on' time of the first pulse phase only; the duration of the symmetric second pulse phase is ignored. This duty cycle is not constant over the 1 kHz to 10 kHz frequency range: for example, the optimal pulse width at 1 kHz (104 microseconds) is not merely ten times the optimal pulse width at 10 kHz (28.5 microseconds). Thus, there is significance to the optimal pulse widths beyond a mere scaling of the frequency.

FIG. 8C shows average patient pain scores at the optimal stimulation parameters for each frequency in the range of 1 kHz to 10 kHz. As noted earlier, patients in the study, prior to receiving SCS therapy, initially reported pain scores with an average of 6.75. After SCS implantation and during the study, and with amplitude and pulse width optimized during the provisional of sub-perception therapy, their average pain scores dropped significantly, to an average score of about 3 for all frequencies tested.

FIG. 9A provides a deeper analysis of the resulting relationship between optimal pulse width and frequency in the frequency range of 1 kHz to 10 kHz. The chart in FIG. 9A shows the average optimal pulse width for the 20 patients in the study at each frequency, along with the standard error resulting from variations between them. These are normalized at each frequency by dividing the standard error by the optimal pulse width, ranging in variations at each frequency between 5.26% and 8.51%. From this, a 5% variance (lower than all computed values) can be assumed as a statistically-significant variance at all frequencies tested.

From this 5% variance, a maximum average pulse width (PW+5%) and a minimum average pulse width (PW+5%) can be calculated for each frequency. For example, the optimal average pulse width PW at 1 kHz is 104 microseconds, and 5% above this value (1.05*104 µs) is 109 µs; 5% below this value (0.95*104) is 98.3 µs. Likewise, the optimal average pulse width AVG(PW) at 4 kHz is 68.0 microseconds, and 5% above this value (1.05*68.0 µs) is 71.4 µs; 5% below this value (0.95*68.0 µs) is 64.6 µs. Thus, a statistically-significant reduction in pain without paresthesia occurs in or on the linearly bounded region 100a of points 102 of (1 kHz, 98.3 µs), (1 kHz, 109 µs), (4 kHz, 71.4 µs), and (4 kHz, 64.6 µs). A linearly bounded region 100b around points 102 is also defined for frequencies greater than or equal to 4 kHz and less than or equal to 7 kHz: (4 kHz, 71.4 µs), (4 kHz, 64.6 µs), (7 kHz, 44.2 µs), (7 kHz, 48.8 µs). A linear bounded region 100c around points 102 is also defined for frequencies greater than or equal to 7 kHz and less than or equal to 10 kHz: (7 kHz, 44.2 µs), (7 kHz, 48.8 µs), (10 kHz, 29.9 µs), (10 kHz, 27.1 µs). Such regions 100 thus comprise information relating frequency and pulse width at which stimulation pulses are formed to provide pain relief without paresthesia in the frequency range of 1 kHz to 10 kHz.

Figure 9B:
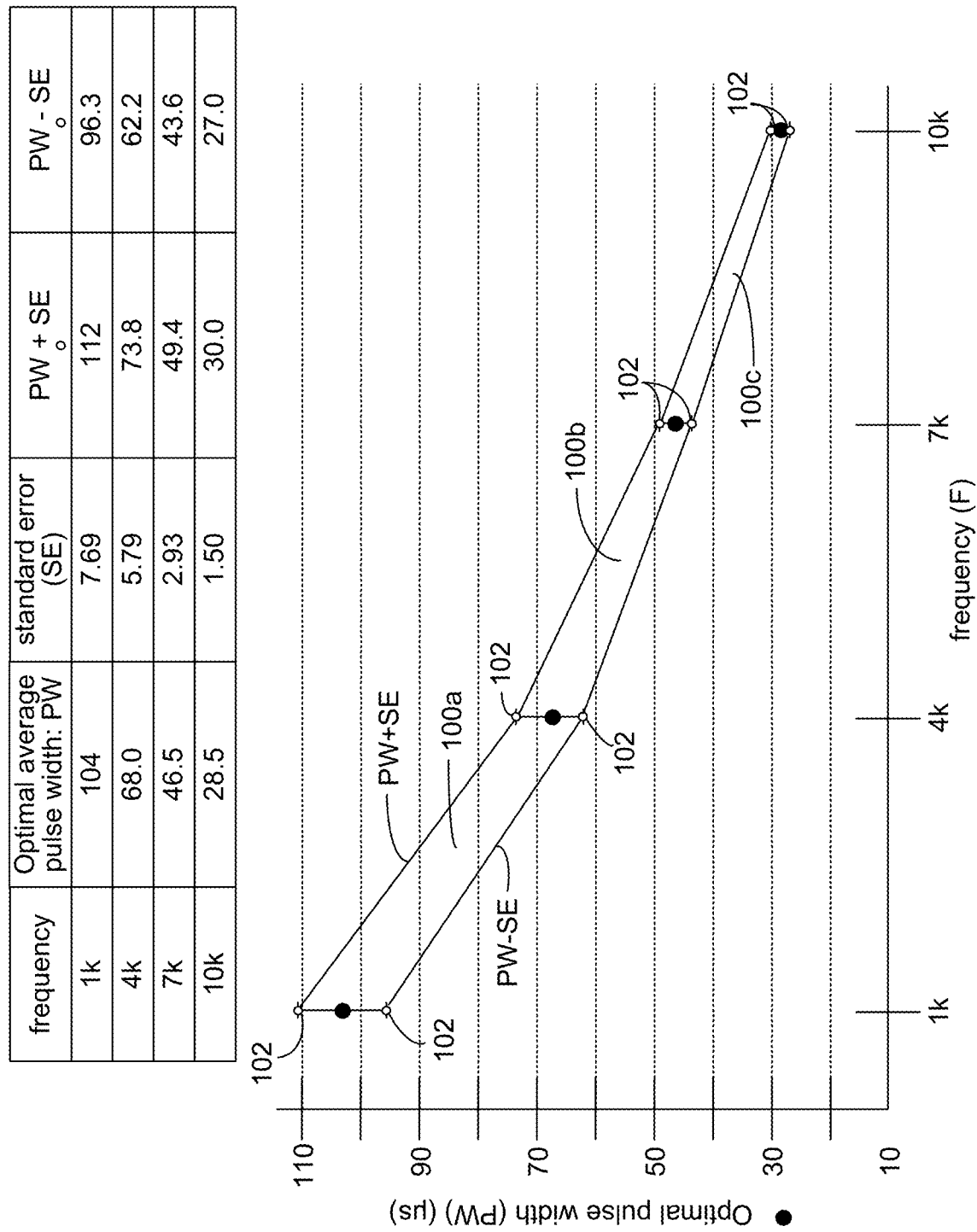

FIG. 9B provides an alternative analysis of the resulting relationship between optimal pulse width and frequency. In this example, regions 100a-100c are defined based upon the standard error (SE) calculated at each frequency. Thus, points 102 defining the corners of the regions 100a-c are simply located at the extent of the SE error bars at each frequency (PW+SE, and PW−SE), even though these error bars are of different magnitudes at each frequency. Thus, a statistically-significant reduction in pain without paresthesia occurs in or on the linearly bounded region 100a of points (1 kHz, 96.3 µs), (1 kHz, 112 µs), (4 kHz, 73.8 µs), and (4 kHz, 62.2 µs). The linear bounded regions 100b and 100c are similar, and because the points 102 defining them are set forth in chart at the top of FIG. 11B, they are not repeated here.

Figure 9C:
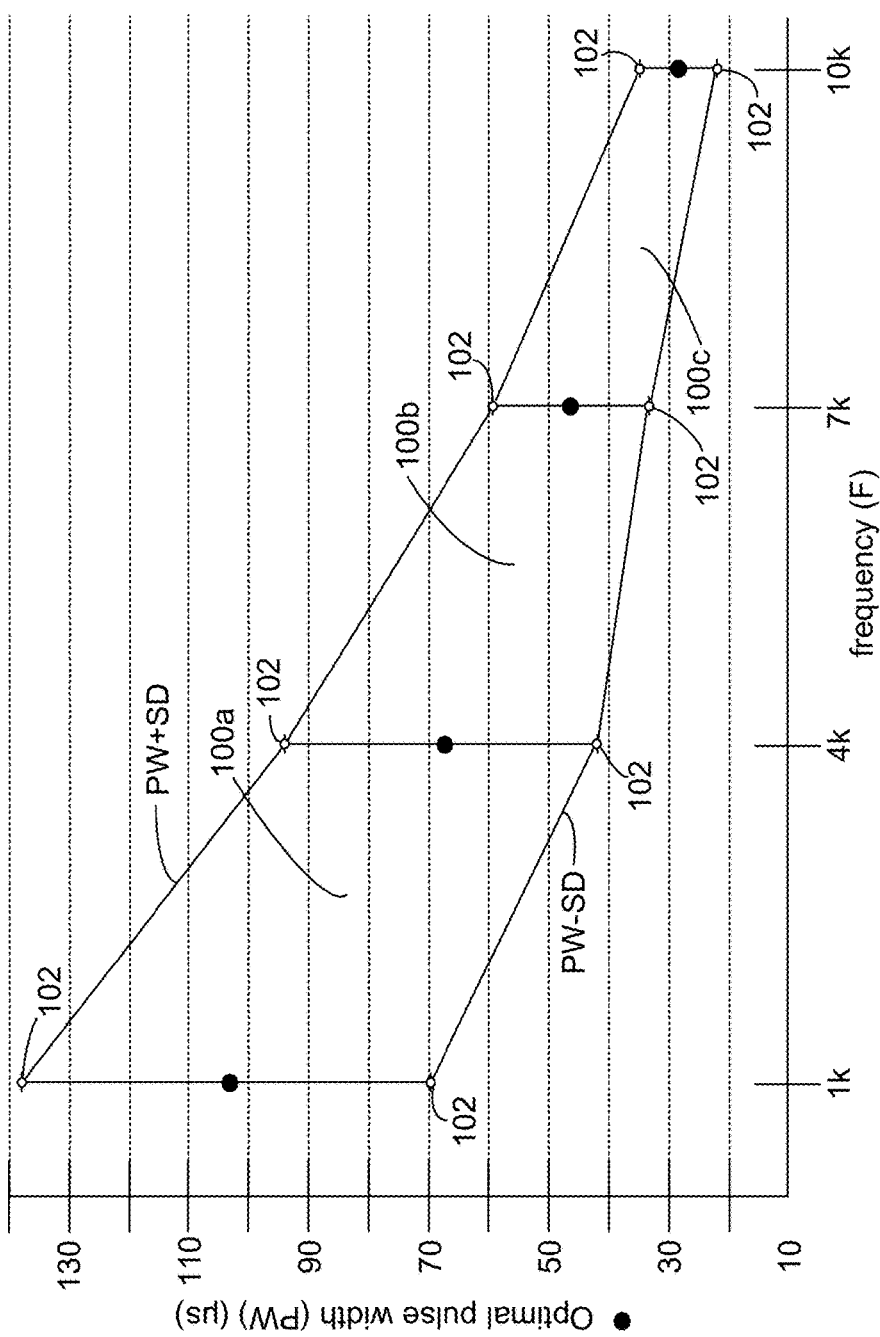

FIG. 9C provides another analysis of the resulting relationship between optimal pulse width and frequency. In this example, regions 100a-100c are defined based upon the standard deviation (SD) calculated at each frequency, which is larger than the standard error (SE) metric used to this point. Points 102 defining the corners of the regions 100a-c are located at the extent of the SD error bars at each frequency (PW+SD, and PW−SD), although points 102 could also be set within the error bars, similar to what was illustrated earlier with respect to FIG. 11A. In any event, a statistically-significant reduction in pain without paresthesia occurs in or on the linearly bounded region 100a of points (1 kHz, 69.6 µs), (1 kHz, 138.4 µs), (4 kHz, 93.9 µs), and (4 kHz, 42.1 µs). The linear bounded regions 100b and 100c are similar, and because the points 102 defining them are set forth in chart at the top of FIG. 11C, they are not repeated here.

More generally, although not illustrated, regions within the frequency range of 1 kHz to 10 kHz where sub-perception efficacy was achieved comprises linearly-bounded region 100a (1 kHz, 50.0 µs), (1 kHz, 200.0 µs), (4 kHz, 110.0 µs), and (4 kHz, 30.0 µs); and/or linearly-bounded region 100b (4 kHz, 110.0 µs), (4 kHz, 30.0 µs), (7 kHz, 30.0 µs), and (7 kHz, 60.0 µs); and/or linearly-bounded region 100c (7 kHz, 30.0 µs), (7 kHz, 60.0 µs), (10 kHz, 40.0 µs), and (10 kHz, 20.0 µs).

In summary, one or more statistically-significant regions 100 can be defined for the optimal pulse width and frequency data taken for the patients in the study to arrive at combinations of pulse width and frequency that reduce pain without the side effect of paresthesia within the frequency range of 1 kHz to 10 kHz, and different statistical measures of error can be used to so define the one or more regions.

FIGS. 10A-10D show the results of testing other patients with sub-perception stimulation therapy at frequencies at or below 1 kHz. Testing of the patients generally occurred after supra-perception sweep spot searching occurred to select appropriate electrodes (E), polarities (P) and relative amplitudes (X %) for each patient, although again the sub-perception electrodes used could vary from those used during the supra-perception sweet spot search (e.g., using MICC). Patients were tested with sub-perception stimulation using symmetric biphasic bipoles, although the form of pulses used during sub-perception therapy could vary.

Figure 10A:
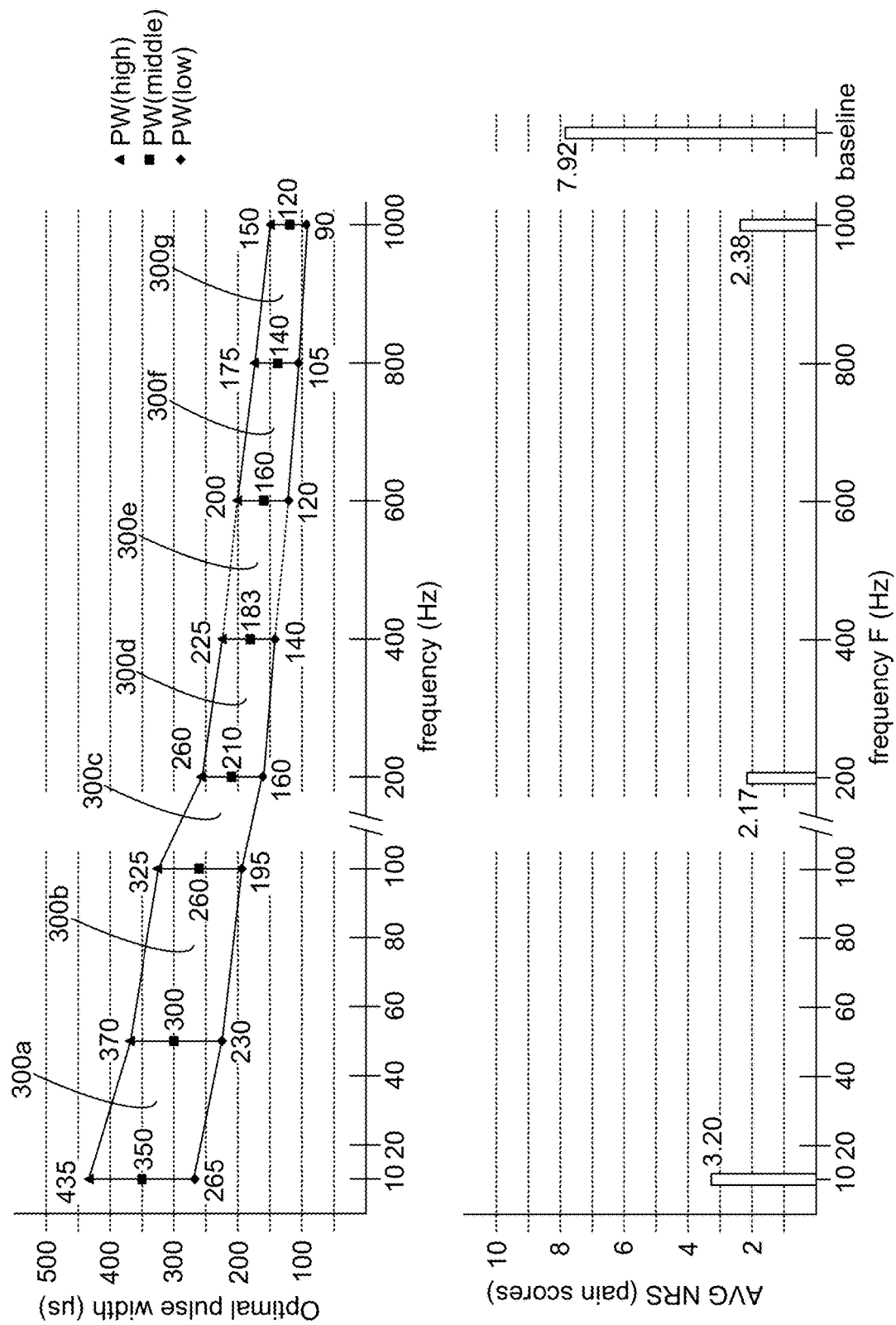
FIGS. 10A-10D show the results of testing other patients with sub-perception stimulation therapy at frequencies at or below 1 kHz.

FIG. 10A shows the relationship between frequency and pulse width at which effective sub-perception therapy was reported by patients for frequencies of 1 kHz and below. Note that the same patient selection and testing criteria described earlier (FIG. 9) can be used when evaluating frequencies at or below 1 kHz, with the frequencies adjusted as appropriate.

As can be seen, at each frequency tested, the optimal pulse width again fell within a range. For example, at 800 Hz, patients reported good results when the pulse width fell within a range of 105-175 microseconds. The upper end of the pulse width range at each frequency is denoted PW(high), while the lower end of the pulse width range at each frequency is denoted PW(low). PW(middle) denotes the middle (e.g., average) of the PW(high) and PW(low) at each frequency. At each of the tested frequencies the amplitude of the current provided (A) was titrated down to sub-perception levels, such that the patient could not feel paresthesia. Typically, the current was titrated to 80% of the threshold at which paresthesia could be sensed. Because each patient's anatomy is unique, the sub-perception amplitude A could vary from patient to patient. The pulse width data depicted comprises the pulse width of only the first phase of the stimulation pulses.

Table 1 below expresses the optimal pulse width versus frequency data of FIG. 10A in tabular form for frequencies at or below 1 kHz, with the pulse widths expressed in microseconds:

TABLE 1

| Frequency (Hz) | PW(low) (µs) | PW(middle) (µs) | PW(high) (µs) |
|---|---|---|---|
| 1000 | 90 | 120 | 150 |
| 800 | 105 | 140 | 175 |
| 600 | 120 | 160 | 200 |
| 400 | 140 | 183 | 225 |
| 200 | 160 | 210 | 260 |
| 100 | 195 | 260 | 325 |
| 50 | 230 | 300 | 370 |
| 10 | 265 | 350 | 435 |

As with the analysis described earlier for frequencies in a range of 1 kHz to 10 kHz (FIGS. 8A-9C), the data may be broken down to define different regions 300$i$ at which effective sub-perception therapy is realized below 1 kHz. For example, regions of effective sub-perception therapy may be linearly bounded between various frequencies and the high and low pulse widths that define effectiveness. For example, at 10 Hz, PW(low)=265 microseconds and PW(high)=435 microseconds. At 50 Hz, PW(low)=230 microseconds and PW(high)=370 microseconds. Therefore, a region 300$a$ that provides good sub-perception therapy is defined by the linearly bounded region of points (10 Hz, 265 µs), (10 Hz, 435 µs), (50 Hz, 370 µs), and (50 Hz, 230 µs). Table 2 defines the points that linearly bind each of the regions 300$a$-300$g$ shown in FIG. 10A:

TABLE 2

| region | Bounded by points (Hz, µs) |
|---|---|
| 300a | (10, 265), (10, 435), (50, 370), (50, 230) |
| 300b | (50, 230), (50, 370), (100, 325), (100, 195) |
| 300c | (100, 195), (100, 325), (200, 260), (200, 160) |
| 300d | (200, 160), (200, 260), (400, 225), (400, 140) |
| 300e | (400, 140), (400, 225), (600, 200), (600, 120) |
| 300f | (600, 120), (600, 200), (800, 175), (800, 105) |
| 300g | (800, 105), (800, 175), (1000, 150), (1000, 90) |

Regions of sub-perception therapeutic effectiveness at frequencies at or below 1 kHz may be defined in other statistically-significant ways, such as those described earlier for frequencies in the range of 1 kHz to 10 kHz (FIGS. 9A-9C). For example, regions 300$i$ may be defined by reference to the pulse width at the middle of the ranges at each frequency, PW(middle). PW(middle) may comprise for example an average optimal pulse width reported by patients at each frequency, rather than a strict middle of an effective range reported by those patients. PW(high) and PW(low) may then be determined as a statistical variance from the average PW(middle) at each frequency, and used to set the upper and lower bounds of effective sub-perception regions. For example, PW(high) may comprise average PW(middle) plus a standard deviation or standard error, or a multiples of such statistical measures; PW(low) may likewise comprise average PW(middle) minus a standard deviation or standard error, or a multiple of such statistical measures. PW(high) and PW(low) may also be determined from average PW(middle) in other ways. For example, PW(high) may comprise average PW(middle) plus a set percentage, while PW(low) may comprise PW(middle) minus a set percentage. In summary, one or more statistically-significant regions 300 can be defined for the optimal pulse width and frequency data at frequencies at or below 1 kHz that reduce pain using sub-perception stimulation without the side effect of paresthesia.

Also shown in FIG. 10A are average patient pain scores (NRS scores) reported by patients when optimal pulse widths are used for different frequencies at 1 kHz or below. Prior to receiving SCS therapy, patients initially reported pain scores with an average of 7.92. After SCS implantation, and using the sub-perception stimulation at optimal pulse widths with the ranges shown at each frequency, the patients' average pain scores dropped significantly. At 1 kHz, 200 Hz, and 10 Hz, patients reported average pain scores of 2.38, 2.17, and 3.20 respectively. Thus clinical significance with respect to pain relief is shown when the optimal pulse widths are used at or below 1 kHz with sub-perception therapy.

Figure 10B:
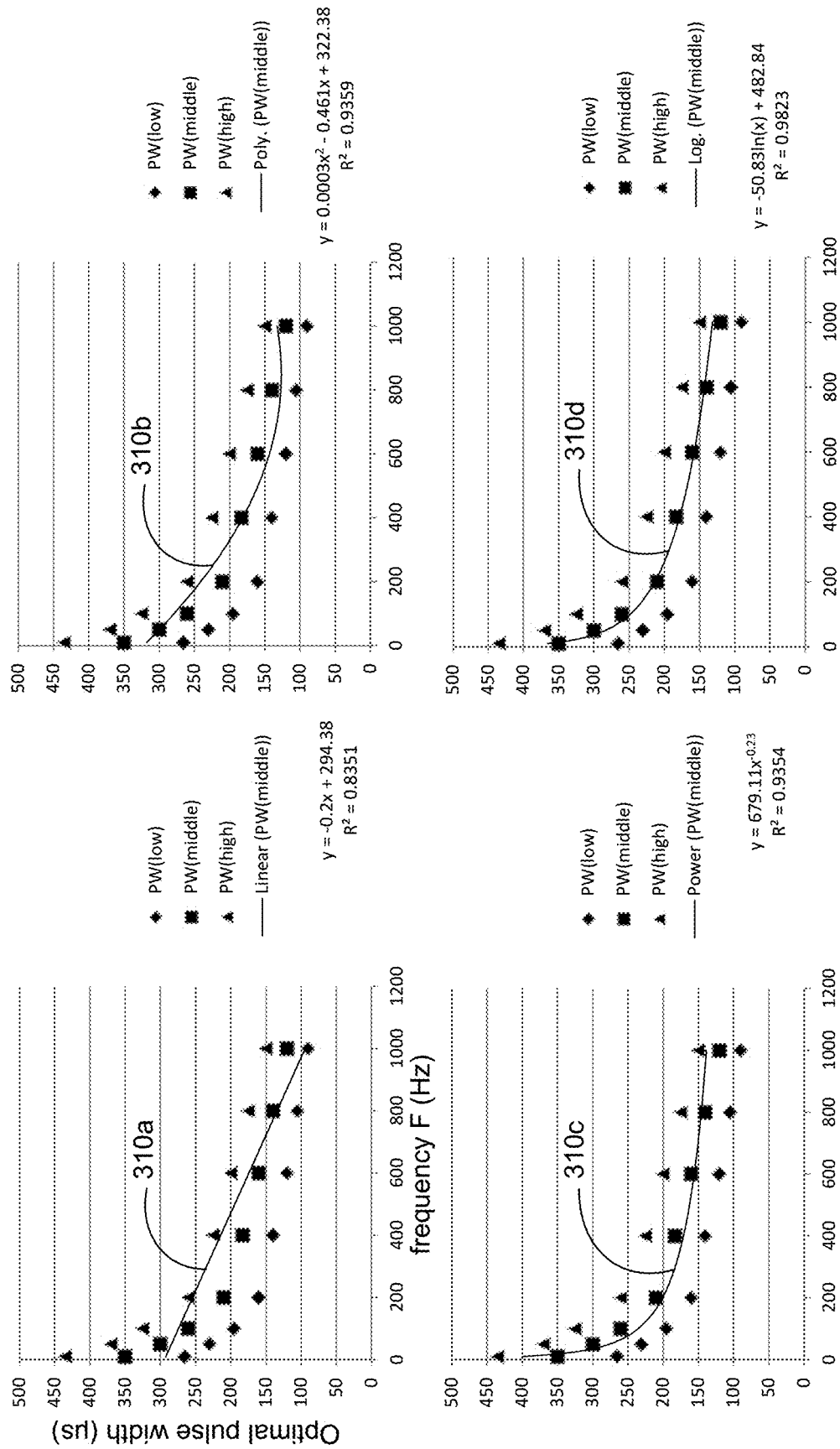

The optimal pulse width versus frequency data of FIG. 10A for frequencies at or below 1 kHz is analyzed in FIG. 10B from the perspective of the middle pulse width, PW(middle) at each frequency (F). As shown, the relationships 310$a$-310$d$ follows statistically significant trends, as evidenced by the various regression models shown in FIG. 12B and summarized in Table 3 below:

TABLE 3

| Regression model | Relationship (PW(middle) in µs) | Correlation coefficient $R^2$ |
|---|---|---|
| Linear (310a) | PW(middle) = −0.2F + 294.4 | 0.835 |
| Polynomial (310b) | PW(middle) = 0.0002$F^2$ − 0.461F + 332.38 | 0.936 |
| Power (310c) | PW(middle) = 679.1$x^{-0.23}$ | 0.935 |
| Logarithmic (310d) | PW(middle) = −50.83ln(F) + 482.8 | 0.982 |

Other fitting methods could be used to establish other information relating frequency and pulse width at which stimulation pulses are formed to provide sub-perception pain relief without paresthesia.

Regression analysis can also be used to define statistically relevant regions such as 300$a$-300$g$ where sub-perception therapy is effective at or below 1 kHz. For example, and although not shown in FIG. 10B, regression can be performed for PW(low) v. F to set a lower boundary of relevant regions 300$i$, and regression can be performed for PW(high) v. F to set an upper boundary of relevant regions 300$i$.

Figure 10C:
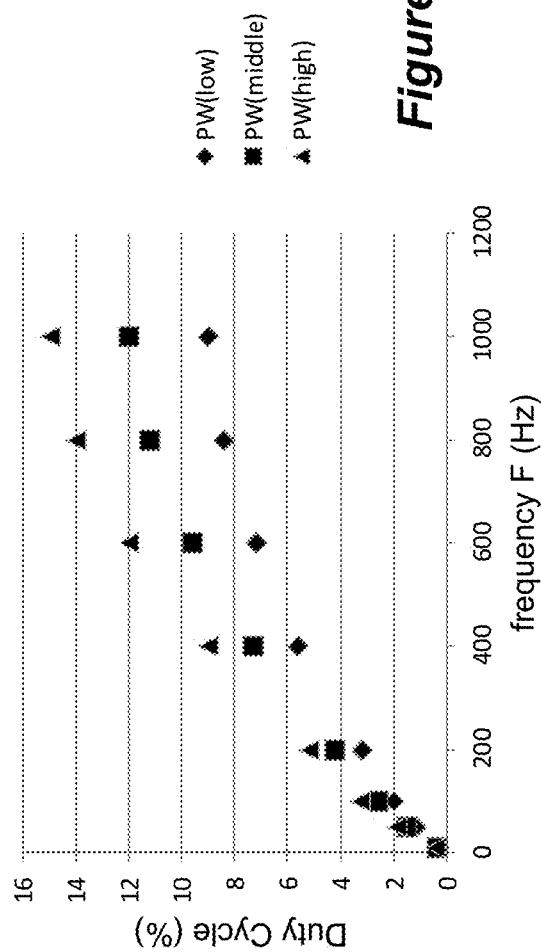

Note that the relationship between optimal pulse width and frequency depicted in FIG. 10A is not simply an expected relationship between frequency and duty cycle (DC), as FIG. 10C shows. As was the case when the 1 kHz to 10 kHz frequency range was tested (FIG. 9A), the duty cycle of the optimal pulse widths is not constant at 1 kHz and below. Again, there is significance to the optimal pulse widths beyond a mere scaling of the frequency. Nonetheless, most of the pulse widths observed to be optimal at 1 kHz and below are greater than 100 microseconds. Such pulse widths are not even possible at higher frequencies. For example, at 10 kHz, both pulse phases have to fit within a 100 us period, so PW longer than 100 are not even possible.

Figure 10D:
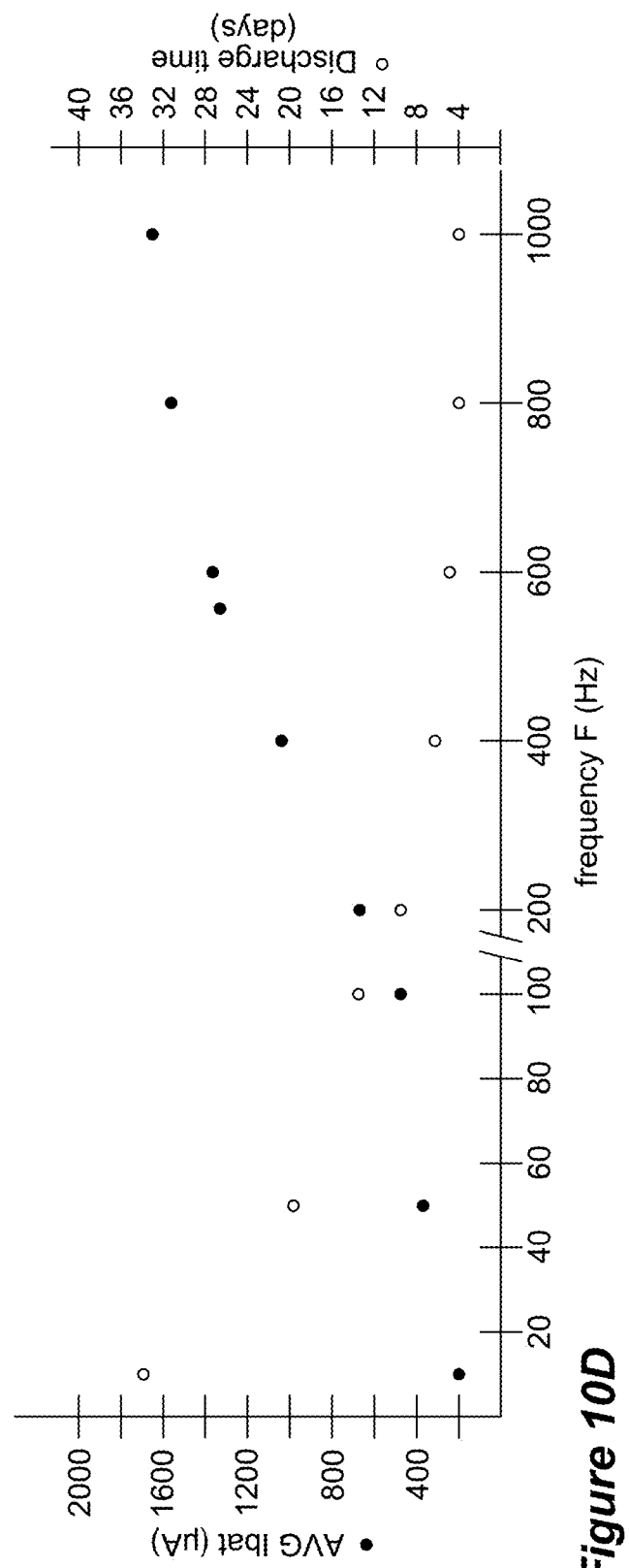

FIG. 10D shows further benefits achieved in using sub-perception at frequencies of 1 kHz and below, namely reduced power consumption. Two sets of data are graphed. The first data set comprises the average current drawn by the battery in the patients' IPG or ETS (AVG Ibat) at each frequency using the optimal pulse width for that patient (FIG. 10A) and the current amplitude A necessary to achieve sub-perception stimulation for that patient (again, this amplitude can vary for each of the patients). At 1 kHz, this average battery current is about 1700 microamps. However, as the frequency is reduced, this average battery current drops, to about 200 microamps at 10 Hz. The second data set looks at power consumption from a different vantage point, namely the number of days that an IPG or ETS with a fully-charged rechargeable battery can operate before recharge is required ("discharge time"). As would be expected based on the average battery current data, the discharge time is lower at higher frequencies when the average battery current is higher (e.g., about 3.9 days at 1 kHz, depending on various charging parameters and settings), and is higher at lower frequencies when the average battery current is lower (e.g., about 34 days at 10 Hz, depending on various charging parameters and settings). This is significant: not only can effective sub-perception therapy be provided at 1 kHz and below when optimal pulse widths are used; power consumptions is greatly lowered, which places less stress on the IPG or ETS, and allows it to operate from longer periods of time. As noted above, excessive power consumption is a significant problem when sub-perception therapy is traditionally used at higher frequencies. Note that the data of FIG. 10D could also be analyzed in terms of mean charge-per-second (MSC), as described earlier for the 1 kHz to 10 kHz data (FIG. 8B).

Once determined, the information 350 relating frequency and pulse width for optimal sub-perception therapy without paresthesia can be stored in an external device used to program the IPG 10 or ETS 40, such as the clinician programmer 50 or external controller 45 described earlier. This is shown in FIG. 13, in which the control circuitry 70 or 48 of the clinician programmer or external controller is associated with region information 100*i* or relationship information 98*i* for frequencies in the 1 kHz to 10 kHz range, and region information 300*i* or relationship information 310*i* for frequencies at or below 1 kHz. Such information can be stored in memory within or associated with the control circuitry. Storing of this information with the external device is useful to assisting the clinician with sub-perception optimization, as described further below. Alternatively, and although not shown, the information relating frequency and pulse width can be stored in the IPG or ETS, thus allowing the IPG or ETS to optimize itself without clinician or patient input.

Figure 11:
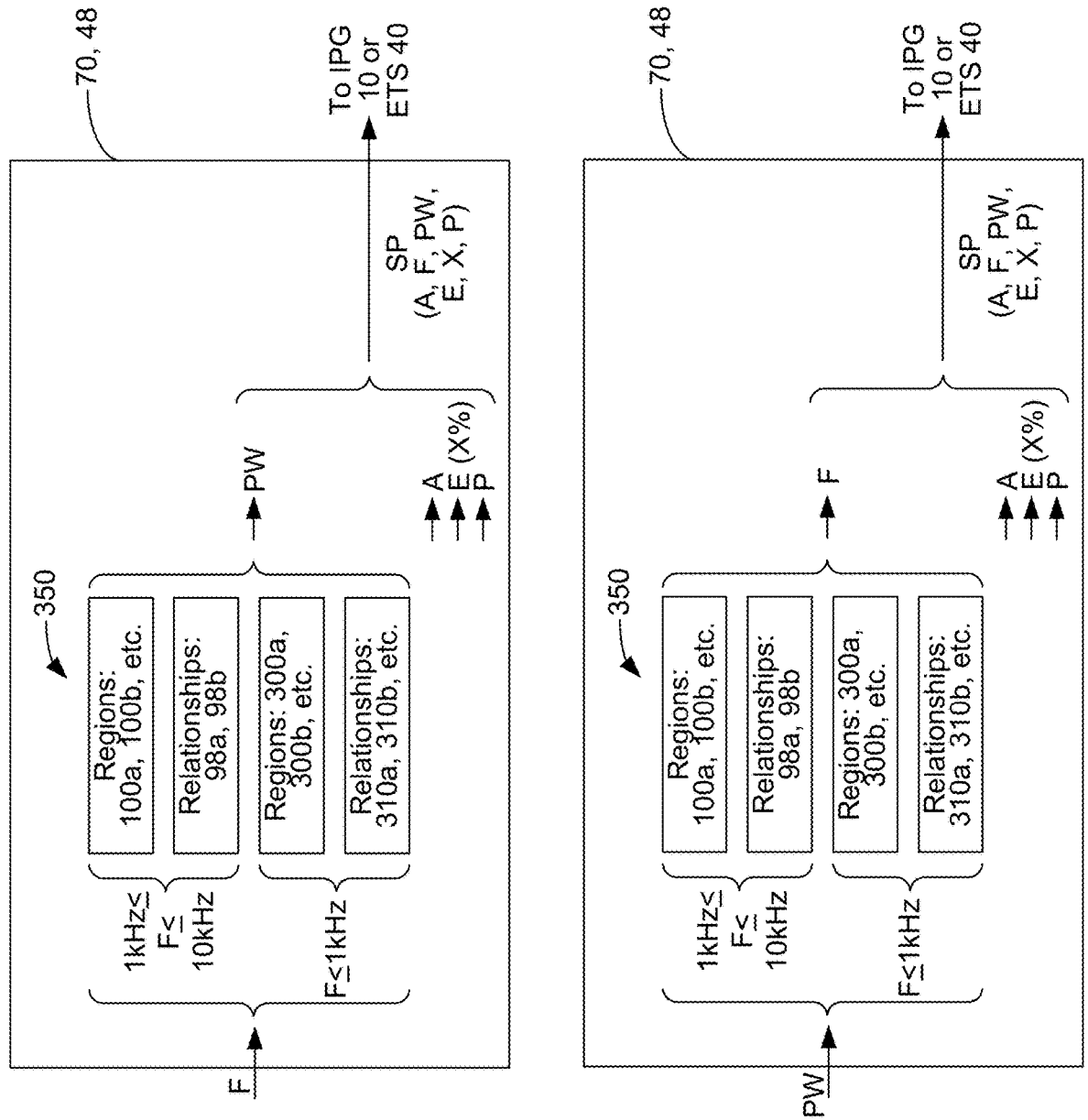
FIG. 11 illustrates an embodiment of a fitting module that may be used to optimize pulse width when frequency is known, or vice versa.

FIG. 11 illustrates an embodiment of a fitting module 350 that may be used to optimize pulse width when frequency is known, or vice versa. The fitting module 350 may be implemented a as software module within a clinician programmer, or may be implemented in the controller of the IPG or ETS. As shown at the top of FIG. 11, the clinician or patient can enter a frequency F into the clinician programmer 50 or external controller 45. This frequency F is passed to the fitting module 350 to determine a pulse width PW for the patient, which is statistically likely to provide suitable pain relief without paresthesia. Frequency F could for example be input to the relationships 98*i* or 310*i* to determine the pulse width PW. Or, the frequency could be compared to the relevant region 100*i* or 300*i* within which the frequency falls. Once the correct region 100*i* or 300*i* is determined, F can be compared to the data in regions to determine a pulse width PW, which may perhaps be a pulse width between the PW+X and PW−X boundaries at the given frequency, as described earlier. Other stimulation parameters, such as amplitude A, active electrodes E, their relative percentage X %, and electrode polarity P can be determined in other manners, such as those described below, to arrive at a complete stimulation program (SP) for the patient. Based on the data from FIG. 10B, an amplitude near 3.0 mA might be a logical starting point, as this amplitude was shown to be preferred by patients in the 1 kHz to 10 kHz range. However, other initial starting amplitudes may be chosen as well, which amplitudes for sub-perception therapy may be dependent on frequency. The bottom of FIG. 11 shows use of the fitting module 350 in reverse—that is to pick a frequency given a pulse width. The system may be configured to allow the user to associate the frequency and pulse width such that when the frequency or pulse width is changed, the other of the pulse width or frequency is automatically changed to correspond to an optimal setting. In some embodiments, associating the frequency and pulse width in this manner can comprise a selectable feature (e.g., in GUI 64) useable when sub-perception programming is desired, and associating the frequency and pulse width can be unselected or unselectable for use with other stimulation modes.

FIG. 12 illustrates a combination sub-perception program 1250 that may include parameter set(s) to provide slow-acting sub-perception neuromodulation 1251 and fast-acting sub-perception neuromodulation 1252. Thus, the combination sub-perception program 1250 may capture positive aspects of both fast-acting and slow-acting sub-perception neuromodulation. Benefits of fast-acting sub-perception neuromodulation includes a faster wash-in transition period, such that it is easier and faster to program. On the flip side, a challenge for slow-acting sub-perception neuromodulation is slower wash-in transition periods, which may make it is slower and harder to program. The set-up of slow-acting sub-perception may require amplitude and field transition. Another benefit of fast-acting sub-perception neuromodulation includes a longer wash-out transition period. A benefit of slow-acting sub-perception neuromodulation is that the anatomically-based programming appears to be less sensitive to lead movements, and thus may require less programming. On the flip side, a challenge for fast-acting sub-perception neuromodulation is that it may be more sensitive to lead movements, such that it may require more reprogramming to keep the field in the desired region. For example, various embodiments deliver a neuromodulation therapy by delivering both a fast-acting sub-perception neuromodulation and a slow-acting sub-perception neuromodulation, wherein the fast-acting neuromodulation has a wash-in transition period less than a first time duration, and the slow-acting sub-perception neuromodulation has a wash-in transition period more than a second time duration, where the second time duration is longer than the first time duration. According to some embodiments, fast-acting sub-perception neuromodulation may have a wash-in transition period less than two hours. For some embodiments, fast-acting sub-perception neuromodulation 1251 may have a wash-in transition period less than 30 minutes. For some embodiments, fast-acting sub-perception neuromodulation 1251 may have a wash-in transition period less than 5 minutes or less than 2 minutes. For some embodiments, fast-acting sub-perception neuromodulation 1251 may have a wash-in transition period less than 60 seconds, or less than 40 seconds, or less than 20 seconds. According to some embodiments, slow-acting 1252 neuromodulation may have a wash-in transition period more than an hour, or more than two hours. According to some embodiments, slow-acting neuromodulation 1252 may have a wash-in transition period more than 6 hours, or more than 12 hours, or more than 18 hours, or more than 24 hours. According to some embodiments, slow-acting neuromodulation 1252 may have a wash-in transition period of two or more days.

Figure 15:
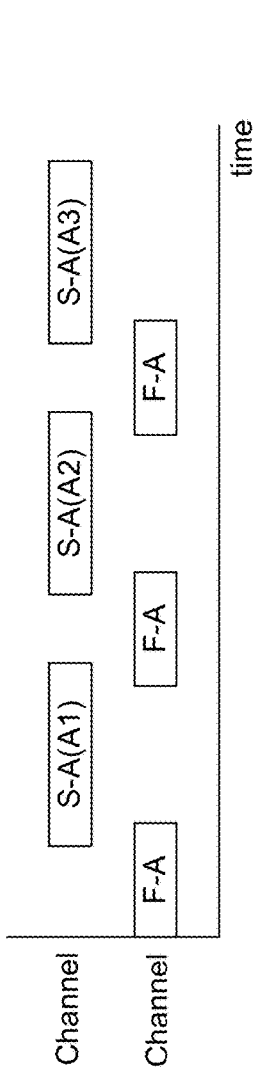

FIGS. 13-15 illustrate examples of timing for a neuromodulation sub-perception therapy that may include delivering slow-acting and fast-action sub-perception neuromodulation in different timing channels. In the timing illustrated in FIG. 13, the slow-acting and fast-acting sub-perception neuromodulation are initiated simultaneously or nearly simultaneously, and the fast-acting sub-perception neuromodulation is terminated before the slow-acting sub-perception neuromodulation. The combination sub-perception therapy may be programmed to implement this timing. In some embodiments, a user interface may be used to receive a user-provided command to initiate and/or terminate either one or both of the slow-acting and fast-acting neuromodulation. Thus, by way of example and not limitation, the fast-acting sub-perception neuromodulation may provide a desired therapeutic effect until the slow-acting sub-perception neuromodulation washes in. In another non-limiting example, the timing may reflect the longer wash-out transition time associated with the fast-acting sub-perception neuromodulation. In the timing illustrated in FIG. 14, the fast-acting sub-perception neuromodulation is delivered multiple times during the slow-acting sub-perception neuromodulation. The longer wash-out transition period of the fast-acting sub-perception neuromodulation may provide a bolus of neuromodulation. In another example, the fast-acting sub-perception neuromodulation may quickly respond to a transient condition that requires additional therapeutic effect. In an example where therapy is delivered to treat pain, the intermittent fast-acting sub-perception neuromodulation may be triggered by a patient or automatically to address times of increased discomfort such as travel times or bedtime when the patient wants to be able to relax to fall asleep. In the timing illustrated in FIG. 15, different slow-acting sub-perception neuromodulation may be delivered. In the illustrated example, the three instances of the slow-acting sub-perception neuromodulation are delivered to different areas (A1, A2, A3). Each instance may correspond to a slow-acting sub-perception neuromodulation parameter set. The fast-acting sub-perception neuromodulation may correspond to, but is not required to correspond to, the same fast-acting sub-perception neuromodulation set. Delivery of the fast-acting sub-perception neuromodulation and delivery of the slow-acting sub-perception neuromodulation may overlap.

Figure 16:
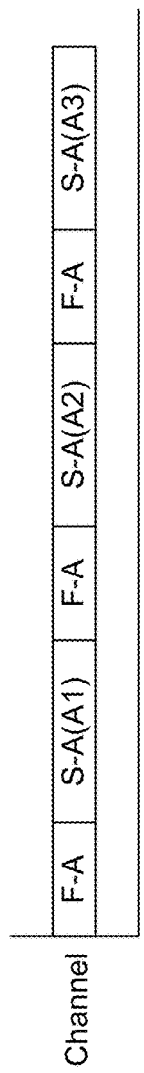
FIG. 16 illustrates an example of timing for a neuromodulation sub-perception therapy that may include delivering slow-acting and fast-action sub-perception neuromodulation in a same timing channel.

FIG. 16 illustrates an example of timing for a neuromodulation sub-perception therapy that may include delivering slow-acting and fast-action sub-perception neuromodulation in a same timing channel. The figure illustrates an instances of fast-action sub-perception neuromodulation followed by an instance of slow-acting sub-perception neuromodulation. The instances of slow-acting sub-perception neuromodulation may be delivered to different areas. The figure illustrates the concatenated instances of different neuromodulation, such that one is terminated when or nearly when another is initiated. Thus, a single waveform pattern on the channel may include a fast-action portion of the waveform pattern and a slow-action portion of the waveform pattern. It is also noted that there may be times without neuromodulation between successive instances of the neuromodulation. The combination sub-perception therapy may be programmed to implement this timing. In some embodiments, a user interface may be used to receive a user-provided command to initiate and/or terminate either one or both of the slow-acting and fast-acting neuromodulation.

Figure 17:
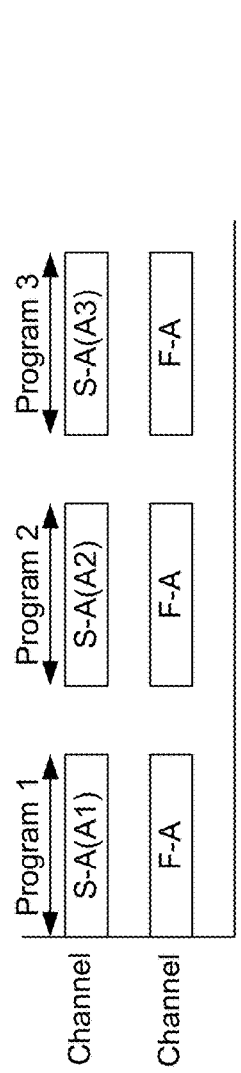
FIGS. 17-18 illustrate examples of sub-perception neuromodulation programs that include delivery of both slow-action and fast-action sub-perception neuromodulation. These programs may be available for selection by the user (e.g. via remote control) or a clinician (e.g. via a programmer) for evaluation.
Figure 18:
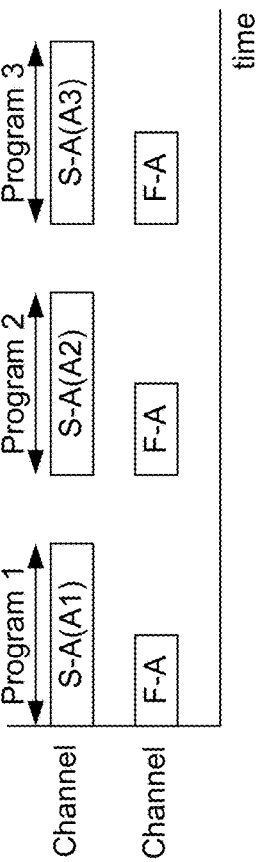

FIGS. 17-18 illustrate examples of sub-perception neuromodulation programs that include delivery of both slow-action and fast-action sub-perception neuromodulation. These programs may be available for selection by the user (e.g. via remote control) or a clinician (e.g. via a programmer) for evaluation. After one neuromodulation program ends, there may be a period of time to allow the neuromodulation to wash-out before the next program begins. The duration of the slow-action sub-perception neuromodulation may be longer than the duration of the fast-action sub-perception neuromodulation, or the duration of both the slow-action and fast-action sub-perception neuromodulation may be the same. Both the slow-action and fast-action sub-perception neuromodulation may be initiated at the same time. As illustrated in these embodiments, each program corresponds to a different slow-action sub-perception neuromodulation parameter set (e.g. different area (A1-A3)). The different slow-action sub-perception neuromodulation parameter set may include different values for other parameters, such as amplitude, pulse width, frequency, etc. and/or may include different waveform patterns. The different programs that are tested may also include different relative timing between the slow-action and fast-action sub-perception neuromodulation. For example, a fast-action sub-perception neuromodulation may be initiated and/or terminated at different times with respect to the delivered slow-action sub-perception neuromodulation for each of the programs. The combination sub-perception therapy may be programmed to implement this timing. In some embodiments, a user interface may be used to receive a user-provided command to initiate and/or terminate either one or both of the slow-acting and fast-acting neuromodulation.

Figure 19:
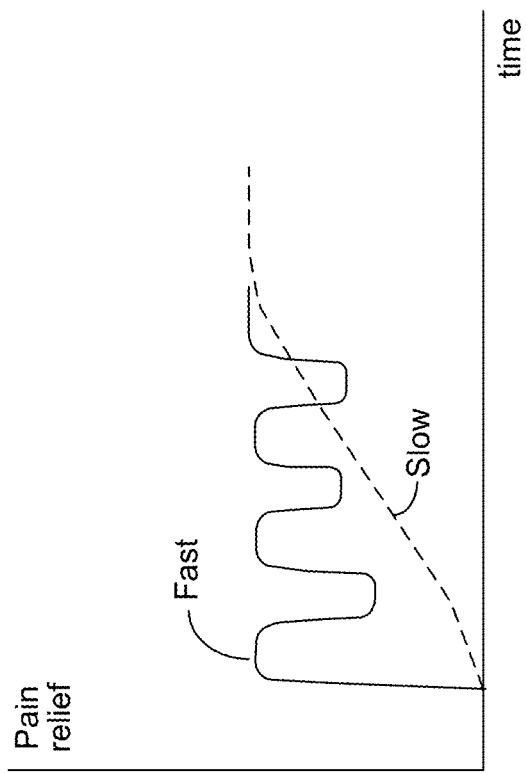
FIG. 19 illustrates an example of a combination sub-perception neuromodulation program.

FIG. 19 illustrates an example of a combination sub-perception neuromodulation program. The fast-action sub-perception neuromodulation has a fast wash-in transition period, as generally illustrated by the steep rising slope; whereas the slow-action sub-perception neuromodulation has a slow wash-in transition period, as generally illustrated by the longer rising slope. The fast-action sub-perception neuromodulation is intermittent, allowing times for reprogramming the parameters. The pain relief attributed to the fast-action sub-perception neuromodulation does not completely wash-out before it is initiated again. Once the slow-action sub-perception neuromodulation completes or nearly completes the wash-in transition period, the fast-action sub-perception neuromodulation may terminate, may continue, or may be adjusted.

Figure 20:
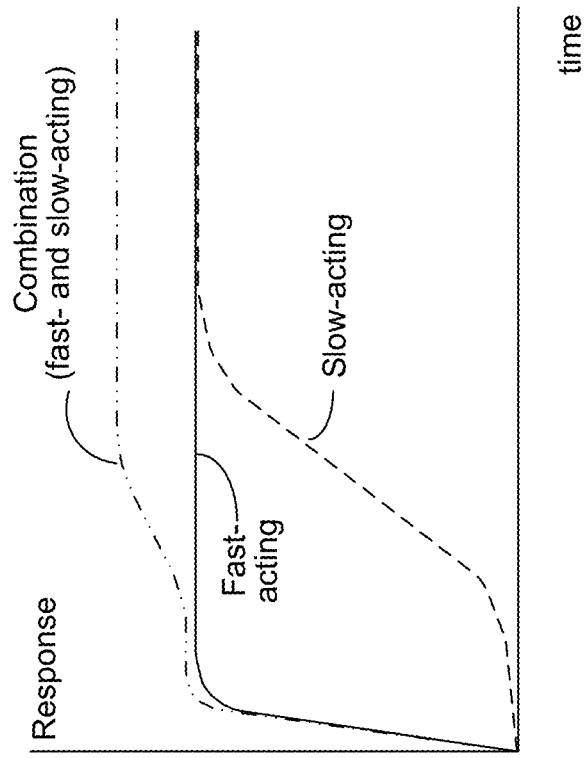
FIG. 20 illustrates an example of a combination sub-perception neuromodulation program that provides additive effects of both the slow-action and fast-action sub-perception neuromodulation.

FIG. 20 illustrates an example of a combination sub-perception neuromodulation program that provides additive effects of both the slow-action and fast-action sub-perception neuromodulation. In the illustration, both the fast-action and slow-action sub-perception neuromodulation are initiated at the same time. The fast-action sub-perception neuromodulation has a short wash-in transition and the slow-action sub-perception neuromodulation has a long wash-in transition period, such that the combination is attributable mostly to the fast-action sub-perception neuromodulation. As the slow-action sub-perception neuromodulation progresses through its wash-in period, it contributes to the overall response of the therapy. Although the effects are additive, it is noted that the contribution may not correspond 1 to 1 to the individual ones of the fast-action and slow-action sub-perception neuromodulation.

Figures 21, 22, 23:
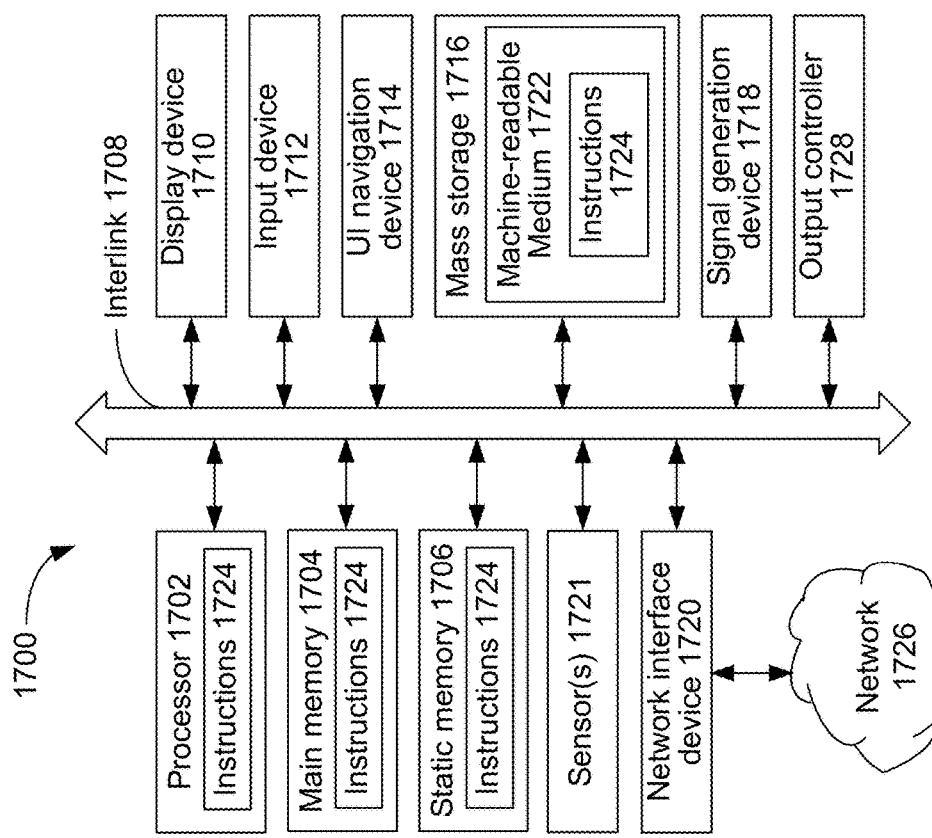
FIGS. 21-22 illustrate examples of neuromodulation programs. Such schedule may be used to test two or more neuromodulation programs, where each of the two or more neuromodulation programs includes programmed modulation parameter sets to control delivery of a slow-acting sub-perception neuromodulation and fast-acting sub-perception neuromodulation.
FIG. 23 is a block diagram illustrating a machine in the example form of a computer system, within which a set or sequence of instructions may be executed to cause the machine to perform any one of the methodologies discussed herein, according to an example embodiment.

FIGS. 21-22 illustrate examples of neuromodulation programs. Such schedule may be used to test two or more neuromodulation programs, where each of the two or more neuromodulation programs includes programmed modulation parameter sets to control delivery of a slow-acting sub-perception neuromodulation and fast-acting sub-perception neuromodulation. The programmed modulation parameter sets may include programmed modulation parameter sets to provide different slow-acting sub-perception neuromodulation. areas. As each program is testing a different slow-acting sub-perception neuromodulation, the duration of the program is sufficient to allow the slow-acting sub-perception neuromodulation to wash-in (e.g. more than 12 hours, or more than 24 hours, or more than two days). The programmed modulation parameter sets may include programmed modulation parameter sets to provide different slow-acting sub-perception neuromodulation parameter values (e.g. amplitudes, pulse widths or frequencies).

FIG. 21 illustrates nine separate programs, where each program includes a parameter set for delivering fast-action sub-perception neuromodulation and another parameter set for delivering slow-action sub-perception neuromodulation. The fast-action sub-perception neuromodulation may be implemented using the same parameter sets. The slow-action sub-perception neuromodulation may be implemented using different parameter sets (e.g. S1-S3 representing areas 1-3, and A1-A3 representing amplitudes 1-3). One of these programs may be implemented after another one of these programs is terminated. Since the fast-acting sub-perception neuromodulation may need to be updated periodically because of its higher spatial sensitivity, it is desirable that updates to the fast-acting sub-perception neuromodulation parameter set replace all fast-acting sub-perception neuromodulation parameter sets for all programs in the schedule (rather than having to replace one program at a time). Such global changes are easier to program by a clinician, and are also well-suited to allow patients to self-steer a fast-acting sub-perception neuromodulation parameter set.

FIG. 22 also illustrates nine separate programs similar to the programs illustrated in FIG. 21. However, each program is separated by a time when only the slow-acting sub-perception neuromodulation is delivered (e.g. the fast-acting sub-perception neuromodulation drops outs). This may provide time to reprogram the fast-acting sub-perception neuromodulation. Intermittently reprogramming the fast-acting sub-perception neuromodulation during the program schedule may include determining a supra-perception neuromodulation parameter set that provides effective supra-perception neuromodulation. The system may respond to a user input (e.g. an auto sub-perception button) by automatically determining a modified fast-acting sub-perception neuromodulation parameter set based on the supra-perception neuromodulation parameter set. While fast-action sub-perception neuromodulation is sensitive in space, they do not seem to have the same sensitivity in amplitude and seem to work well in a small fixed range below the perception threshold (e.g. 80-90% of the perception threshold. The button or command may be implemented in either or both of the clinician's programmer or remote control. Actuation of the button may take a supra-perception neuromodulation parameter set (e.g. paresthesia area or program), and crate a sub-perception version simply by reducing the amplitude (e.g. 85% of the perception threshold). For example, a patient may self-steer the field and amplitude using a remote control or joystick until the feel paresthesia at the desired location. Upon saving, the button may be used to save a sub-perception version of the program or area (which may be a global area).

FIG. 23 is a block diagram illustrating a machine in the example form of a computer system, within which a set or sequence of instructions may be executed to cause the machine to perform any one of the methodologies discussed herein, according to an example embodiment. For example, the machine may be the electronic device that implements the neuromodulation programs or the electronic device that creates the programs. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be a personal computer (PC), a tablet PC, a hybrid tablet, a personal digital assistant (PDA), a mobile telephone, an implantable pulse generator (IPG), an external remote control (RC), a User's Programmer (CP), or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Similarly, the term "processor-based system" shall be taken to include any set of one or more machines that are controlled by or operated by one or more processors (e.g., a computer) to individually or jointly execute instructions to perform any one or more of the methodologies discussed herein.

An example of a computer system includes at least one processor (e.g., a central processing unit (CPU), a graphics processing unit (GPU) or both, processor cores, compute nodes, etc.), a main memory and a static memory, which communicate with each other via a link (e.g., bus). The computer system may further include a video display unit, an alphanumeric input device (e.g., a keyboard), and a user interface (UI) navigation device (e.g., a mouse). In one embodiment, the video display unit, input device and UI navigation device are incorporated into a touch screen display. The computer system may additionally include a storage device (e.g., a drive unit), a signal generation device (e.g., a speaker), a network interface device, and one or more sensors (not shown), such as a global positioning system (GPS) sensor, compass, accelerometer, or another sensor. It will be understood that other forms of machines or apparatuses (such as IPG, RC, CP devices, and the like) that are capable of implementing the methodologies discussed in this disclosure may not incorporate or utilize every component depicted in FIG. 16 (such as a GPU, video display unit, keyboard, etc.).

The storage device includes a machine-readable medium on which is stored one or more sets of data structures and instructions (e.g., software) embodying or utilized by any one or more of the methodologies or functions described herein. The instructions may also reside, completely or at least partially, within the main memory, static memory, and/or within the processor during execution thereof by the computer system, with the main memory, static memory, and the processor also constituting machine-readable media.

While the machine-readable medium is illustrated in an example embodiment to be a single medium, the term "machine-readable medium" may include a single medium or multiple media (e.g., a centralized or distributed database, and/or associated caches and servers) that store the one or more instructions. The term "machine-readable medium" shall also be taken to include any tangible (e.g., non-transitory) medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions may further be transmitted or received over a communications network using a transmission medium via the network interface device utilizing any one of a number of well-known transfer protocols (e.g., HTTP or Bluetooth®). Examples of communication networks include a local area network (LAN), a wide area network (WAN), the Internet, mobile telephone networks, plain old telephone (POTS) networks, and wireless data networks (e.g., Wi-Fi, 3G, and 4G LTE/LTE-A or 5G networks). The term "transmission medium" shall be taken to include any intangible medium that is capable of storing, encoding, or carrying instructions for execution by the machine, and includes digital or analog communications signals or other intangible medium to facilitate communication of such software.

The above detailed description is intended to be illustrative, and not restrictive. The scope of the disclosure should, therefore, be determined with references to the appended claims, along with the full scope of equivalents to which such claims are entitled.

The invention claimed is:

1. A method, comprising:
   delivering a spinal cord neuromodulation therapy by delivering both a fast-acting sub-perception neuromodulation and a slow-acting sub-perception neuromodulation to a spinal cord of a patient using one or more electrodes implanted adjacent to the spinal cord, wherein the fast-acting neuromodulation has a wash-in transition period less than a first time duration, and the slow-acting sub-perception neuromodulation has a wash-in transition period more than a second time duration, the second time duration being longer than the first time duration.

2. The method of claim 1, wherein the neuromodulation therapy is to treat chronic pain.

3. The method of claim 1, wherein the delivering both the fast-acting sub-perception neuromodulation and the slow-acting sub-perception neuromodulation includes delivering the fast-acting sub-perception neuromodulation using a timing channel and delivering the slow-acting sub-perception neuromodulation using the timing channel.

4. The method of claim 1, wherein the delivering both the fast-acting sub-perception neuromodulation and the slow-acting sub-perception neuromodulation includes delivering the fast-acting sub-perception neuromodulation using a timing channel and delivering the slow-acting sub-perception neuromodulation using a different timing channel.

5. The method of claim 1, wherein the delivering both the fast-acting sub- perception neuromodulation and the slow-acting sub-perception neuromodulation includes initiating the fast-acting sub-perception neuromodulation and the slow-acting sub-perception neuromodulation together.

6. The method of claim 1, wherein the delivering both the fast-acting sub-perception neuromodulation and the slow-acting sub-perception neuromodulation includes initiating the fast-acting sub-perception neuromodulation before or after initiating the slow-acting sub-perception neuromodulation.

7. The method of claim 1, wherein the delivering both the fast-acting sub-perception neuromodulation and the slow-acting sub-perception neuromodulation includes terminating the fast-acting sub-perception neuromodulation before terminating the slow-acting sub-perception.

8. The method of claim 1, wherein the delivering both the fast-acting sub-perception neuromodulation and the slow-acting sub-perception neuromodulation includes intermittently delivering the fast-acting sub-perception neuromodulation multiple times during the slow-acting sub-perception neuromodulation.

9. The method of claim 1, wherein a duration of the fast-acting sub-perception neuromodulation is shorter than a duration of the slow-acting sub-perception neuromodulation.

10. The method of claim 1, further comprising testing two or more neuromodulation programs according to a program schedule, wherein each of the two or more neuromodulation programs includes programmed modulation parameter sets to control delivery of the slow-acting sub-perception neuromodulation and the fast-acting sub-perception neuromodulation.

11. The method of claim 10, wherein the programmed modulation parameter sets include programmed modulation parameter sets to provide different slow-acting sub-perception neuromodulation areas.

12. The method of claim 10, wherein the program schedule is configured for use to deliver slow-acting sub-perception neuromodulation to individual ones of the different slow-acting sub-perception neuromodulation areas for a duration longer than 12 hours.

13. The method of claim 10, wherein the programmed modulation parameter sets include programmed modulation parameter sets to provide different slow-acting sub-perception neuromodulation amplitudes.

14. The method of claim 10, further comprising intermittently reprogramming the fast-acting sub-perception neuromodulation during the program schedule, wherein the intermittently reprogramming includes determining a supra-perception neuromodulation parameter set that provides effective supra-perception neuromodulation, and responding to a user input by automatically determining a modified fast-acting sub-perception neuromodulation parameter set based on the supra-perception neuromodulation parameter set.

15. The method of claim 1, further comprising terminating the fast-acting sub-perception neuromodulation in response to a user input.

16. The method of claim 1, further comprising terminating the slow-acting sub-perception neuromodulation in response to a user input.

17. The method of claim 1, wherein the delivering the neuromodulation therapy includes responding to a user input by initiating the fast-acting sub-perception neuromodulation or initiating the slow-acting sub-perception neuromodulation.

18. A neuromodulation system for use with electrodes to modulate a volume of neural tissue, comprising:
- a waveform generator configured to be electrically connected to the electrodes and provide an electrical waveform through at least some of the electrodes to provide a spinal cord neuromodulation therapy, wherein the electrodes are configured to be implanted adjacent to a spinal cord of a patient; and
- a controller configured to use a program to control the waveform generator to deliver the neuromodulation therapy by delivering both a fast-acting sub-perception neuromodulation and a slow-acting sub-perception neuromodulation to the spinal cord of the patient, wherein the fast-acting neuromodulation has a wash-in transition period less than a first time duration, and the slow-acting sub-perception neuromodulation has a wash-in transition period more than a second time duration, the second time duration being longer than the first time duration.

19. A non-transitory machine-readable medium including instructions, which when executed by a machine, cause the machine to configure a program for a neurostimulator that is capable of providing a spinal cord neurostimulation therapy, the instructions causing the machine to configure the program to cause the neurostimulator to:
- deliver the neuromodulation therapy by delivering both a fast-acting sub-perception neuromodulation and a slow-acting sub-perception neuromodulation to a spinal cord of a patient using one or more electrodes implanted adjacent to the spinal cord,
- wherein the fast-acting neuromodulation has a wash-in transition period less than a first time duration, and the slow-acting sub-perception neuromodulation has a wash-in period more than a second time duration, the second time duration being longer than the first time duration.

* * * * *